(12) United States Patent
Shipp et al.

(10) Patent No.: US 12,239,302 B2
(45) Date of Patent: Mar. 4, 2025

(54) VESSEL SEALING DEVICE

(71) Applicant: Cyndrx, LLC, Brentwood, TN (US)

(72) Inventors: John I. Shipp, Jacksonville, FL (US); Dennis Wayne Lawson, Jr., Republic, MO (US)

(73) Assignee: CYNDRX LLC, Brentwood, TN (US)

( * ) Notice: Subject to any disclaimer, the term of this patent is extended or adjusted under 35 U.S.C. 154(b) by 730 days.

(21) Appl. No.: 17/093,529

(22) Filed: Nov. 9, 2020

(65) Prior Publication Data

US 2021/0401417 A1    Dec. 30, 2021

Related U.S. Application Data

(63) Continuation-in-part of application No. 16/253,110, filed on Jan. 21, 2019, now Pat. No. 10,869,656, which is a continuation of application No. 14/852,539, filed on Sep. 12, 2015, now Pat. No. 10,182,803, which is a continuation of application No. 13/746,276, filed on Jan. 21, 2013, now Pat. No. 9,131,931.

(60) Provisional application No. 63/108,154, filed on Oct. 30, 2020.

(51) Int. Cl.
A61B 17/00    (2006.01)
A61B 90/00    (2016.01)

(52) U.S. Cl.
CPC ............ *A61B 17/0057* (2013.01); *A61B 2017/00623* (2013.01); *A61B 2017/00659* (2013.01); *A61B 90/03* (2016.02); *A61B 2090/037* (2016.02)

(58) Field of Classification Search
CPC ...... A61B 17/0057; A61B 2017/00575; A61B 2017/00579; A61B 2017/00584; A61B 2017/00592; A61B 2017/00597; A61B 2017/00588; A61B 2017/00601; A61B 2017/00606; A61B 2017/0061; A61B 2017/00615; A61B 2017/00619; A61B 2017/00623; A61B 2017/00628; A61B 2017/00632; A61B 2017/00637; A61B 2017/00641; A61B 2017/00646; A61B 2017/0065; A61B 2017/00654; A61B 2017/00659; A61B 2017/00663; A61B 2017/00668; A61B 2017/00672; A61B 2017/00676

See application file for complete search history.

(56) References Cited

U.S. PATENT DOCUMENTS

| | | |
|---|---|---|
| 5,342,393 A | 8/1994 | Stack |
| 5,350,399 A | 9/1994 | Erlebacher et al. |
| 5,620,461 A | 4/1997 | Muijs Van De Moer et al. |
| 6,022,351 A | 2/2000 | Bremer et al. |
| 6,045,569 A | 4/2000 | Kensey et al. |

(Continued)

OTHER PUBLICATIONS

International Search Report, Feb. 4, 2021; 2 pages.
International Written Opinion; Feb. 4, 2021; 5 pages.

*Primary Examiner* — Katherine H Schwiker
(74) *Attorney, Agent, or Firm* — Michael L Leetzow

(57) ABSTRACT

A device and a method for sealing an opening in the wall of a blood vessel is provided. The device includes pushing mechanism, a shaft fixedly connected to the pushing mechanism, a seal assembly attached to the distal end of the shaft, and a pushing rod also engaging the seal assembly, the pushing mechanism moving the pushing rod from a first position to a second position.

10 Claims, 40 Drawing Sheets

(56) References Cited

U.S. PATENT DOCUMENTS

| | | | |
|---|---|---|---|
| 6,090,130 A | 7/2000 | Nash et al. | |
| 6,860,895 B1 | 3/2005 | Akerfeldt et al. | |
| 7,175,646 B2 | 1/2007 | Brenneman et al. | |
| 7,250,057 B2 | 7/2007 | Forsberg | |
| 7,335,220 B2 | 2/2008 | Khosravi et al. | |
| 7,488,340 B2 | 2/2009 | Kauphusman et al. | |
| 7,597,705 B2 | 10/2009 | Forsberg et al. | |
| 7,618,438 B2 | 11/2009 | White et al. | |
| 7,850,710 B2 | 12/2010 | Huss | |
| 7,931,670 B2 | 4/2011 | Fiehler et al. | |
| 7,988,706 B2 | 8/2011 | Forsberg | |
| 8,029,533 B2 | 10/2011 | Bagaoisan et al. | |
| 8,048,108 B2 | 11/2011 | Sibbitt, Jr. et al. | |
| 8,075,589 B2 | 12/2011 | Pipenhagen et al. | |
| 8,080,034 B2 | 12/2011 | Bates et al. | |
| 8,128,632 B2 | 3/2012 | Paris et al. | |
| 8,128,652 B2 | 3/2012 | Paprocki | |
| 8,128,653 B2 | 3/2012 | McGuckin, Jr. et al. | |
| 2001/0007077 A1 | 7/2001 | Ginn et al. | |
| 2002/0002386 A1 | 1/2002 | Ginn et al. | |
| 2003/0078598 A1 | 4/2003 | Ginn et al. | |
| 2006/0195123 A1 | 8/2006 | Ginn et al. | |
| 2006/0195124 A1 | 8/2006 | Ginn et al. | |
| 2006/0265007 A1 | 11/2006 | White et al. | |
| 2006/0271078 A1 | 11/2006 | Modesitt | |
| 2007/0060895 A1 | 3/2007 | Sibbitt et al. | |
| 2007/0088388 A1* | 4/2007 | Opolski | A61B 17/0057 606/213 |
| 2007/0112358 A1* | 5/2007 | Abbott | A61B 17/0057 606/142 |
| 2007/0185529 A1 | 8/2007 | Coleman et al. | |
| 2008/0109030 A1 | 5/2008 | Houser et al. | |
| 2008/0243182 A1 | 10/2008 | Bates et al. | |
| 2009/0254119 A1 | 10/2009 | Sibbett, Jr. et al. | |
| 2010/0087854 A1 | 4/2010 | Stopek et al. | |
| 2010/0217311 A1* | 8/2010 | Jenson | A61B 17/0057 606/213 |
| 2010/0305601 A1 | 12/2010 | Karbowniczek et al. | |
| 2011/0066181 A1 | 3/2011 | Jenson et al. | |
| 2012/0022585 A1 | 1/2012 | Atanasoska et al. | |
| 2014/0025103 A1 | 1/2014 | Hundertmark et al. | |
| 2015/0265271 A1* | 9/2015 | Galligan | A61B 17/0401 606/148 |

* cited by examiner

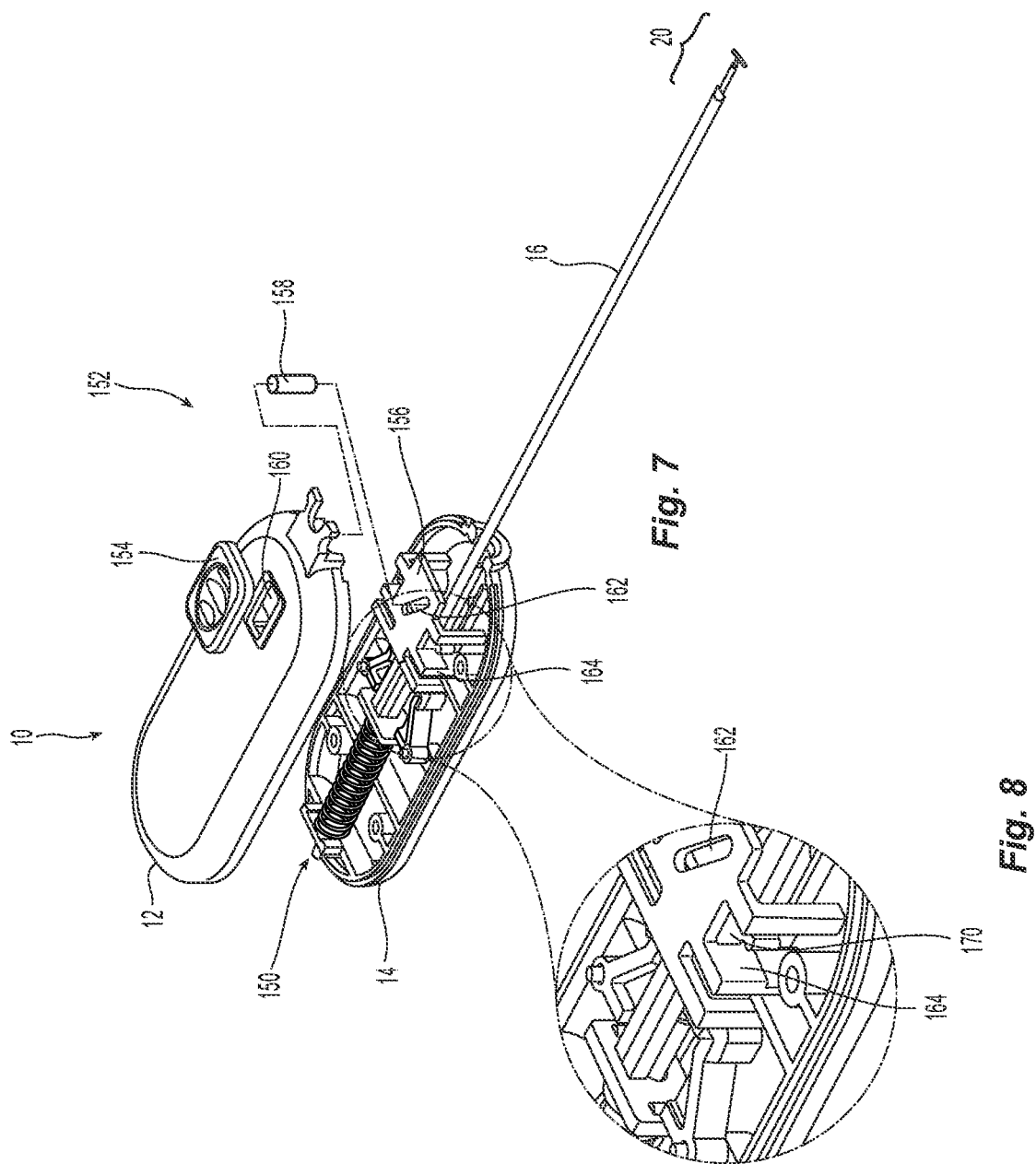

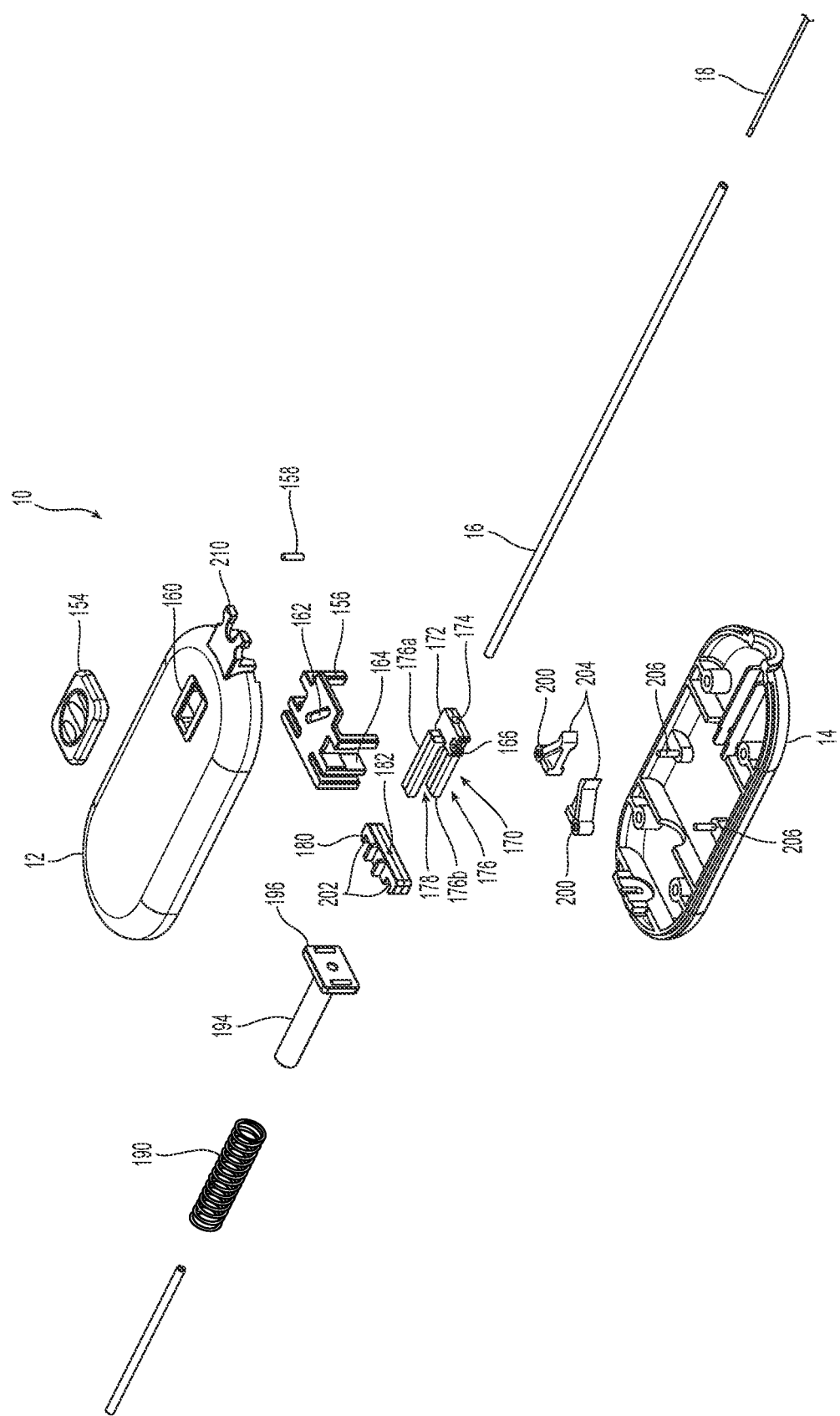

VESSEL SEALING DEVICE

This application is a continuation application of and claims priority to U.S. patent application Ser. No. 13/746,276, filed Jan. 21, 2013, to U.S. patent application Ser. No. 14/852,539, filed on Sep. 12, 2015, to U.S. patent applicant Ser. No. 16/253,110, filed on Jan. 21, 2019, and to U.S. Patent Application Ser. No. 63/108,154, filed on Oct. 30, 2020, the contents of which are hereby incorporated by reference in their entirety.

BACKGROUND OF THE INVENTION

Field of the Invention

The present invention relates generally to a sealing device for the closure of puncture holes in blood vessels and, in particular, to a sealing device that does not require a sheath change and is simple with a single action feature to fire the device.

Technical Background

For many diagnostic and interventional procedures it is necessary to access arteries or veins. Vessel access is accomplished either by direct vision or percutaneously. In either case, the target vessel is punctured with a hollow needle containing a tracer wire. When the intravascular positioning of the tracer wire has been verified, the hollow needle is removed leaving the tracer wire. Next, a sheath containing a dilator is pushed in over the tracer wire. The dilator enlarges the puncture opening to facilitate the insertion of the larger diameter sheath into the blood vessel. The sheath usually consists of a hollow tube with an open distal end and a hemostatic valve at a proximal end, which remains outside the body and blood vessel. The hemostatic valve is made of a compliant material and is designed in such a way as to allow devices such as catheters to be inserted and withdrawn from the blood vessel with minimal blood loss. After the sheath has been inserted into the blood vessel, the dilator is removed leaving a clear passageway in the sheath for the catheter. The sheath is removed from the blood vessel after the procedure is finished resulting in bleeding at the puncture site that must be staunched.

Traditionally, pressure is applied to the puncture site to allow time for the blood to clot thereby stopping the bleeding. Depending on the amount of anticoagulants that may have been administered to the patient during and prior to the procedure, the time pressure must be maintained varies from 15 minutes to more than an hour. Once bleeding has stopped, a pressure bandage is placed over the site of the puncture in an attempt to protect the integrity of the clot. The pressure bandage must remain in place for some time, usually from 8 to 24 hours. During this period of time the patient must remain in bed, sometimes requiring an overnight hospital stay.

To shorten the length of time required for the patient to become ambulatory and to lessen complications sometimes arising from the traditional method, several closure devices have been developed. One such device, as described in U.S. Pat. No. 5,620,461, a foldable sheet with an attachment thread is inserted into the opening in the blood vessel and an arresting element is applied over the attachment element against the outside of the blood vessel. Another such device is described in U.S. Pat. Nos. 6,045,569 and 6,090,130, and includes an absorbable collagen plug cinched down against an absorbable intervascular anchor via an absorbable suture. The anchor has an elongated rectangular shape that requires it to be inserted into the puncture wound with its longitudinal axis parallel to the sheath axis. This requires it to be rotated ninety degrees after insertion so that blood flow obstruction is minimized. A specially designed sheath is necessary to assure proper rotation, thus resulting in an otherwise unnecessary sheath change. The long dimension of the anchor is thus larger than the cannula inside diameter (ID) and the width is smaller than the ID. The collagen plug is in an elongated state prior to deployment and is forced into a ball shape via a slipknot in the suture, which passes through the collagen, and a tamper that applies a distal force to it. The anchor acts as a support for the suture cinch which forces the collagen ball shape up against the exterior vessel wall and the anchor. Blood flow escaping around the anchor is slowed down and absorbed by the collagen material and thus forms a clotting amalgamation outside the blood vessel that is more stable than the traditional method of a standalone clot. The added robustness of the amalgamation clot allows earlier ambulation of the patient.

The device raises several issues. It is not a true sealing device but rather a clotting enhancement device, as opposed to a device with two flat surfaces exerting sealing pressure on both the interior and exterior of the blood vessel, a much more reliable technique. In either case bleeding occurs during the time between removal of the sheath and full functionality of the deployed device. Thus "instant" sealing pressure from two flat surfaces is desirable over a method that relies to any extent on clotting time. One such device is disclosed by Bates et. al. in 8,080,034. The '034 device comprises an internal sealing surface pivoting on a rigid post to accommodate the longitudinal dimension of the seal inside the sheath ID. The exterior seal (second clamping member) is slidable along the rigid post and pivotal such that it, along with the internal seal, sandwiches the wall of the blood vessel via a locking ratchet. One problem with this design is that the pivoting feature increases the cross-sectional dimension of the seal thus requiring a larger diameter sheath than would be otherwise needed. In addition, the pivoting internal seal has no means to assure that the seal pivots to the correct sealing position as the ratchet closes. This could cause the internal seal to exit the blood vessel in the collapsed configuration as the user withdraws the deploying device.

The seals are release by the user cutting the suture thread in the device described in 6,045,569.

It is known that the opening in the blood vessel closes to some extent after the sheath is removed thus allowing smaller seal surfaces than would otherwise be required. What is less known is that the opening does not close as quickly as a truly elastic material such as natural rubber. For this reason seal surfaces of closure devices that are activated in less than a second, or perhaps even longer, after sheath removal must be physically larger than the sheath outside diameter to avoid embolization of the seals because of the delayed vessel closure. The design of seals that are deployed through a sheath ID with dimensions larger than the sheath OD upon deployment is a challenge since the preferred material for seals are bio-absorbable and thus have limited mechanical properties.

The '569 device requires removing the catheter sheath and replacing it with a custom sheath prior to deployment, resulting in addition blood loss. The tamping force used to deploy the collagen against the anchor is left to the surgeon's feel sometimes resulting in inadequate deployment and other times resulting in the collagen being pushed through the puncture wound, into the blood vessel along with the anchor.

Inadequate tamping results in excessive bleeding with the potential for painful hematoma and over tamping can result in a surgical procedure to remove the device from the blood vessel lumen. In addition, the absorption rate of the suture, the collagen, and the anchor may be different owing to the fact that they are formed from different materials, sometimes resulting in the detachment of the anchor, which can move freely in the blood stream and become lodged in the lower extremities of the body, again requiring surgical removal.

It is worth noting that the prior art device, 6,045,569, relies on clotting and is not a true vessel seal. U.S. Patent Publication No. 20060265007 discloses an automatic tamping system that is usable on devices such as those described in U.S. Pat. Nos. 6,045,569 and 6,090,130, to automate certain aspects of deployment, but it fails to provide a way for automatically severing the cinching suture and detaching the applicator from the implanted seal components. In addition the automatic tamping means is complex, adding cost and reducing reliability.

U.S. Patent Publication No. 20190175160 provides a solution to many of these problems but does not allow for positive location of the vessel wall owing to the automatic nature of the device that deploys the seal assembly when the firing force is exceeded. This can occur when the assembly is retracted toward the vessel wall caused by friction of the inner lumen element dragging on the interior wall of the vessel, catching on plaque or other obstructions, resulting in embolization of the entire seal assembly and no hemostasis. In addition, the seal assembly of the '160 application does not provide for a feature to assure the sandwich force is consistent device to device, regardless of the patient's body mass index (BMI).

It would be desirable therefore to provide a vessel-sealing device that actually seals the blood vessel and does not rely on the clotting of the blood. It is also desirable to provide a closure device that is deployable through the catheter sheath with minimal steps requiring less than 2 minutes for hemostasis. It would be also desirable to provide a reliable vessel-sealing device the deployment efficacy of which is independent of the surgeon's feel, i.e. automatic deployment and automatic release of the seals from the deployment instrument

SUMMARY OF THE INVENTION

The present invention is directed to a device for sealing an opening in the wall of a blood vessel, the blood vessel having an interior wall surface, exterior wall surface, and a lumen, the device includes a pushing rod, the pushing rod having an opening therealong, a shaft disposed within at least a portion of the opening of the pushing rod, a pusher, the pusher fixedly attached to the pushing rod, a bottom cover and a top cover, a button extending through the top cover and engaging the pusher, and a seal assembly having a first portion and a second portion, the seal assembly operatively attached at the first portion to the distal end of the shaft, the seal assembly configured to engage the interior wall surface and the exterior wall surface of the blood vessel, wherein the pushing rod operatively engages the seal assembly at the second portion and is movable relative to the shaft, the pushing rod moving from a first position to a second position in response to the button moving distally causing the first portion and the second portion of the seal assembly to move relative to one another.

In some embodiments, the shaft is attached to at least one of the top and the bottom cover.

In some embodiments, the pusher has a foot and two arms, the arms engaging a first groove in the top cover at a proximal end of the opening in first status and a second groove in the top cover at a distal end of the slot in a second status.

In other embodiments, a predetermined force on the button causes the arms to move out of the first groove and into the second groove.

In yet another aspect, the invention is directed to device for sealing an opening in the wall of a blood vessel, the blood vessel having an interior wall surface, exterior wall surface, and a lumen, the device that includes a pusher with arms extending in a first direction and a foot extending in a second direction, a shaft extending between a proximal end and a distal end, the shaft extending within a portion of a pushing rod, a seal assembly having a first portion and a second portion, the seal assembly operatively attached at the first portion to the distal end of the shaft, the seal assembly configured to engage the interior wall surface and the exterior wall surface of the blood vessel, and the pushing rod operatively engaging the seal assembly at the second portion and movable relative to the shaft, the pusher moving the pushing rod from a first position to a second position in response to a button associated with the pusher thereby causing the first portion and the second portion of the seal assembly to move relative to one another.

In yet another aspect, the invention is directed to a device for sealing an opening in the wall of a blood vessel, the blood vessel having an interior wall surface, exterior wall surface, and a lumen, the device includes a pushing assembly, a shaft disposed within at least a portion of the pushing assembly, a bottom cover and a top cover, a button extending through the top cover and engaging a portion of the pushing assembly, and a seal assembly having a first portion and a second portion, the seal assembly operatively attached at the first portion to the distal end of the shaft, the seal assembly configured to engage the interior wall surface and the exterior wall surface of the blood vessel, wherein the pushing assembly operatively engages the seal assembly at the second portion, the pushing assembly moving from a first position to a second position causing the first portion and the second portion of the seal assembly to move relative to one another.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description of the present embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention and together with the description serve to explain the principles and operations of the invention.

BRIEF DESCRIPTION OF THE DRAWINGS

FIG. 7 is a front perspective view of the sealing device with the top handle half removed;

FIG. 8 is a perspective partial view of the safety latch;

FIG. 9 is an exploded view of the sealing device of FIG. 1;

DETAILED DESCRIPTION OF THE PREFERRED EMBODIMENTS

Figure 1:
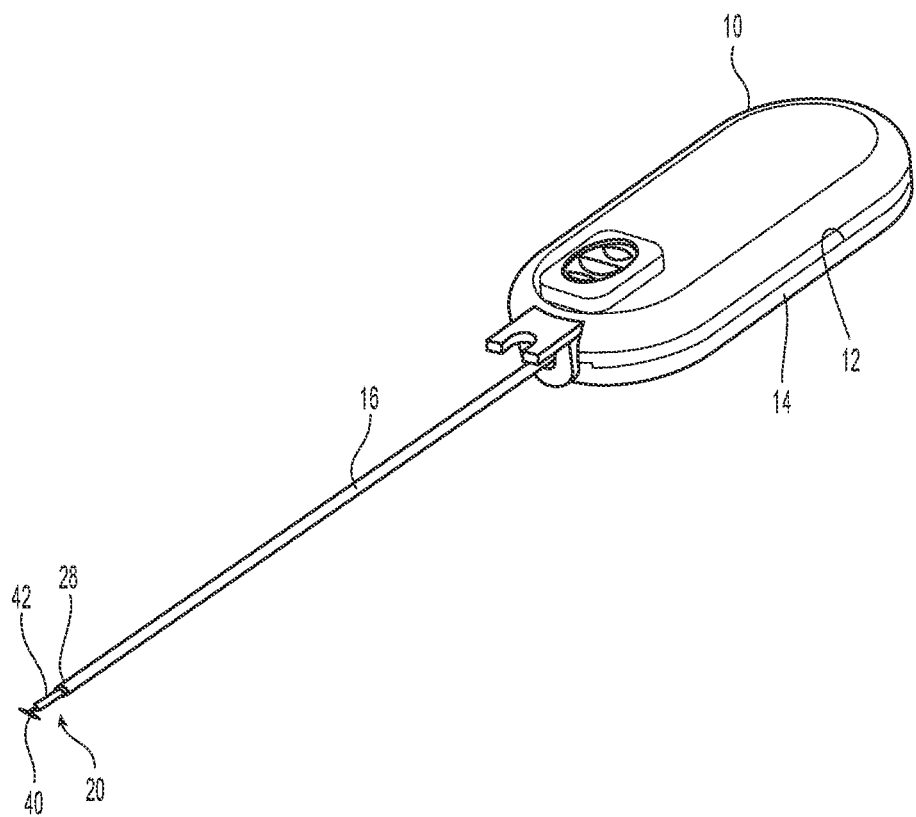
FIG. 1 is a perspective view of one embodiment of a sealing device according to the present invention.

Reference will now be made in detail to the present preferred embodiment(s) of the invention, examples of which are illustrated in the accompanying drawings. Whenever possible, the same reference numerals will be used throughout the drawings to refer to the same or like parts.

Figure 2:
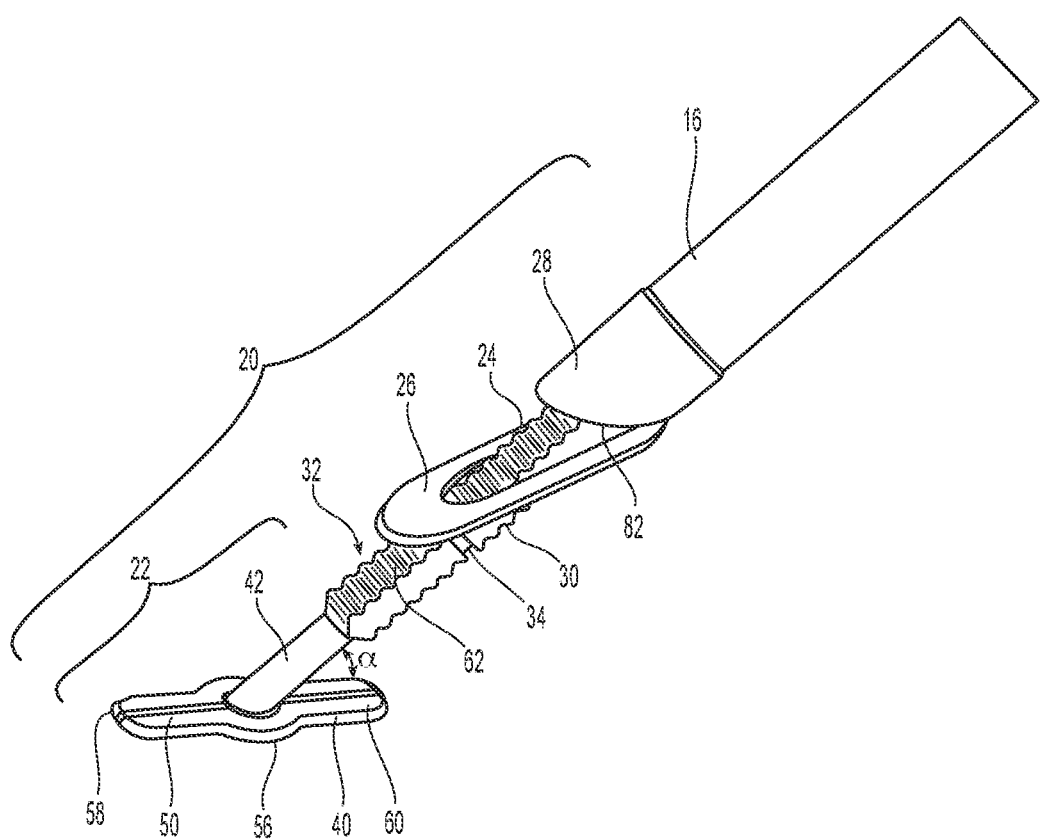
FIG. 2 is a perspective view of a portion of the sealing device of FIG. 1 illustrating the seal assembly thereof.
Figure 3A:
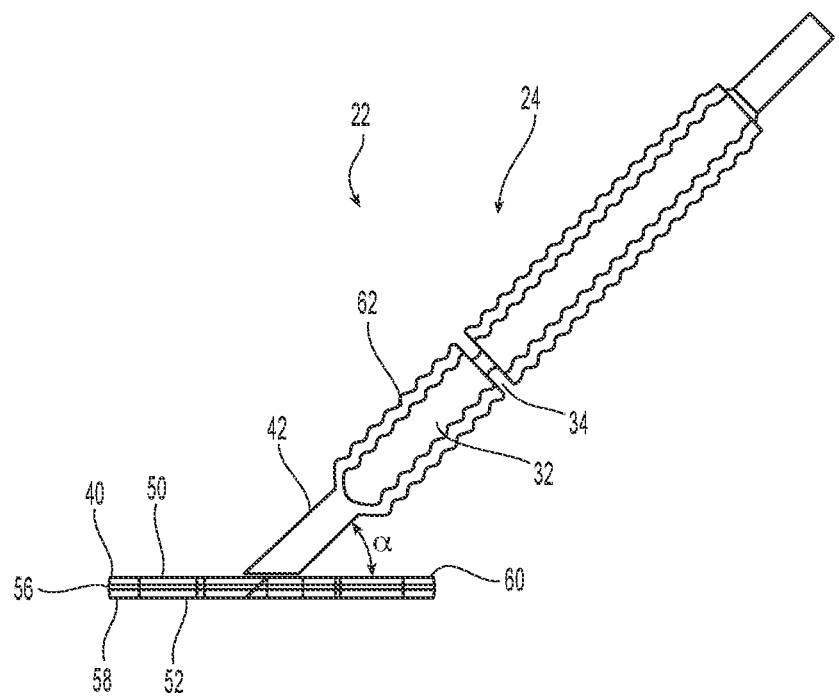
FIG. 3A is a side plan view of the first sealing element and the shaft.
Figure 3B:
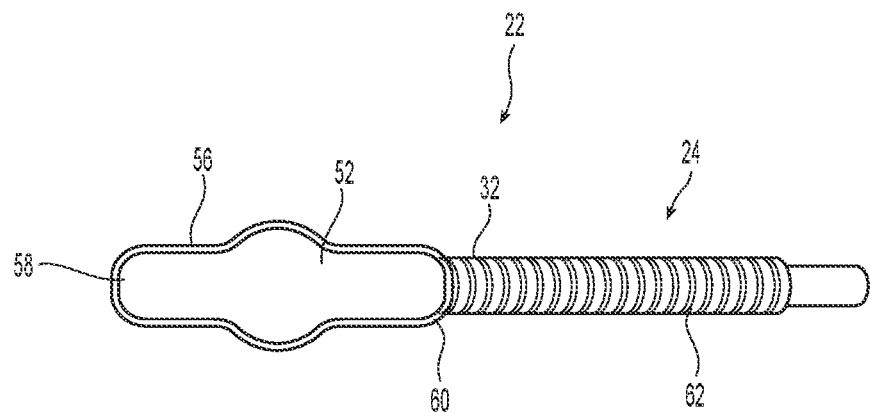
FIG. 3B is a bottom plan view of the first sealing element and the shaft.
Figure 15:
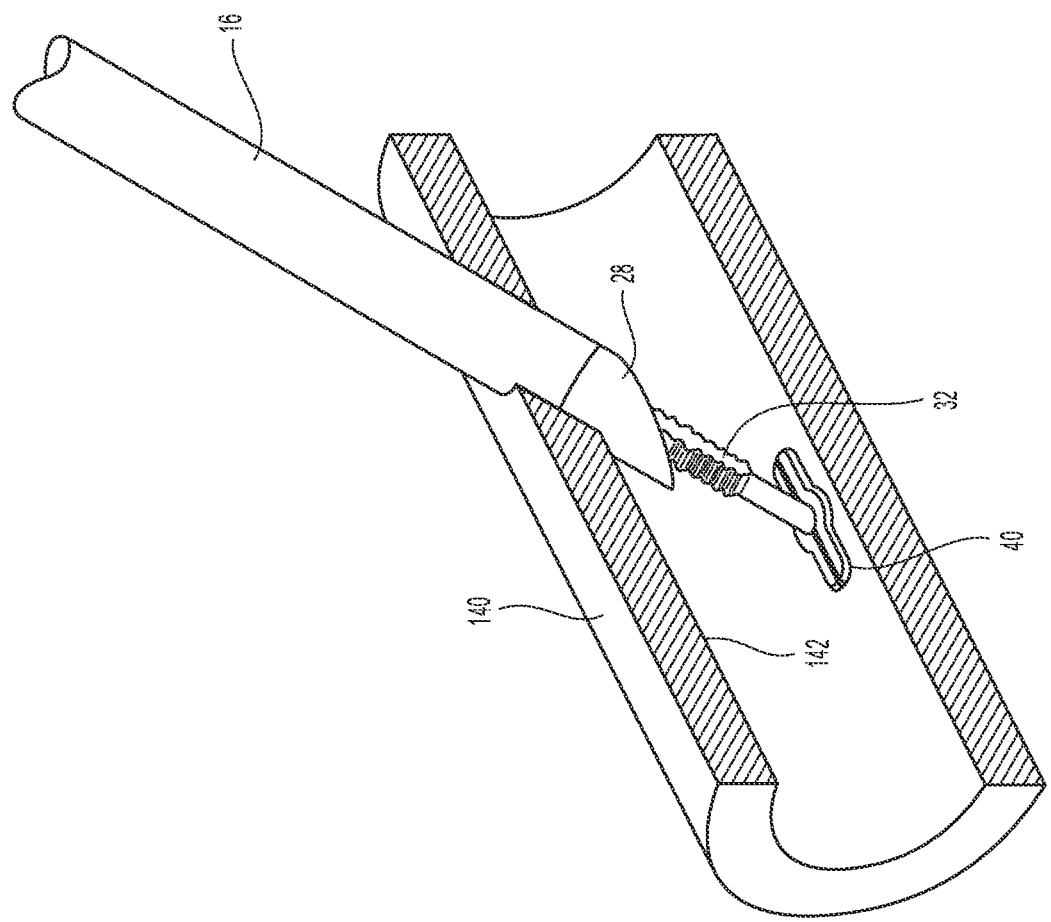
FIG. 15 is partial cross section view of a blood vessel with the sealing device inserted therein.
Figure 16:
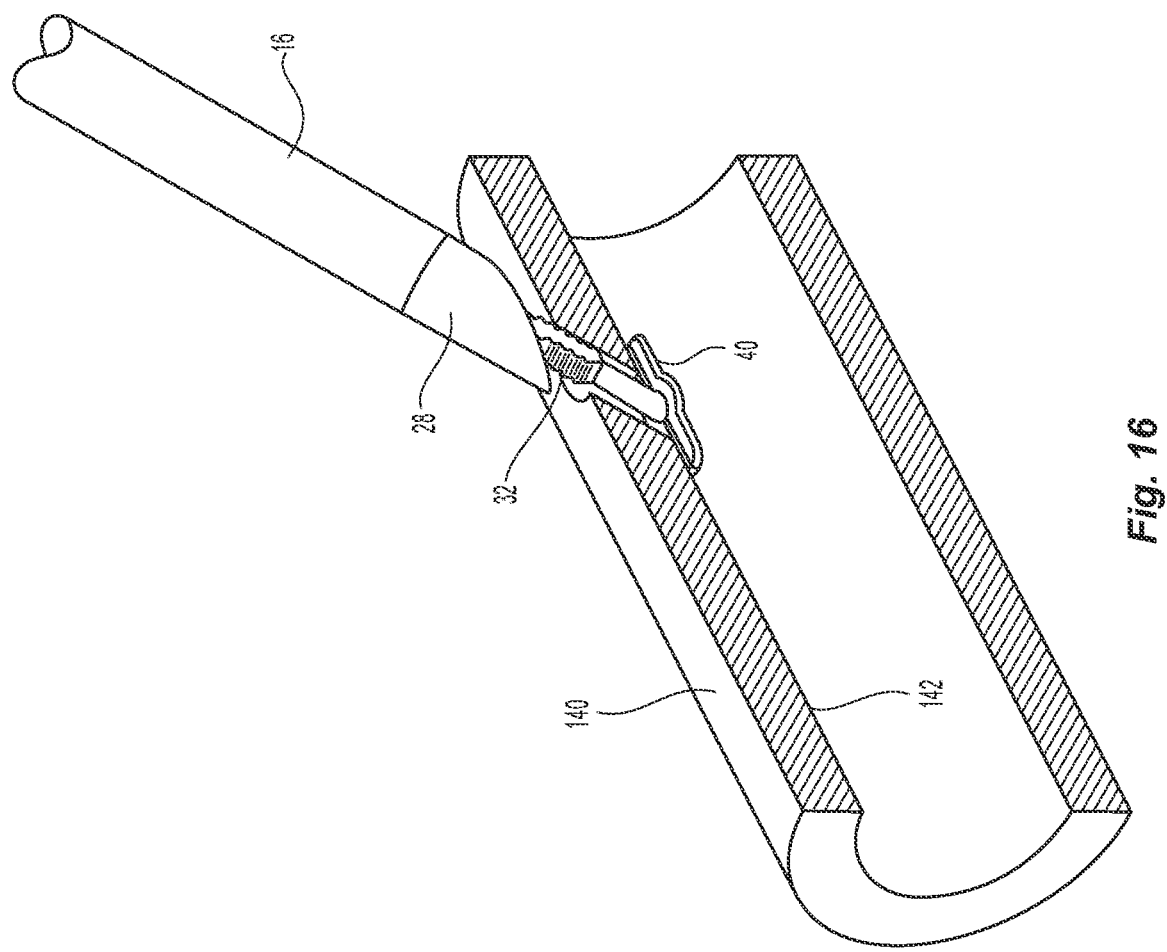
FIG. 16 is perspective view of the sealing device inserted into the blood vessel just before the sealing device is activated.

Referring to FIGS. 1 and 2, closure device 10 is illustrated as having two handle halves 12,14 that house an automatic mechanism, described in more detail below, which is coupled to the seal assembly 20 by a flexible pusher rod 16 and a flexible shaft 18. See FIG. 6. Seal assembly 20 has a first sealing element 22, a knobbed rigid shaft 24, an outer floating element 26, and a second sealing element 28. Knobbed, rigid shaft 24 has a proximal section 30 and a distal section 32 separated by a weakened notch feature 34, which is configured to separate seal assembly 20 from the rest of the closure device 10 once the automatic deployment and sealing process is complete. The length of the distal section 32 of knobbed shaft 24 is dictated by the thickness of the blood vessel wall that can be accommodated. See FIG. 15. The first sealing element 22 also has a distal section 40 configured to interface with the inside wall of a vessel to be sealed, a knobbed, rigid distal shaft section 32 (which is a part of the knobbed, rigid shaft 24), and ankle section 42 joining the distal section 40 to the knobbed, rigid distal shaft section 32. The ankle section 42 is attached to distal section 40 at an angle α, which is preferably at an angle of about 45°. Although other angles may be used, the value of angle α may cause other values of the seal assembly to be changed, as discussed in detail below.

More detailed views of the first sealing element 22 and the knobbed rigid shaft 24 are illustrated in FIGS. 3A-3D. The first sealing element 22 has the distal section 40, ankle section 42 and the knobbed, rigid distal shaft section 32. The distal section 40 has a proximal or top surface 50, a bottom surface 52 and an outer peripheral surface 56. The proximal or top surface 50 is preferably configured to engage the interior wall surface 142 of the blood vessel 140 (see FIG. 15), which means that the top surface 50 is preferably flat. However, the top surface 50 can be of any configuration (e.g., flat, convex, etc.) and still come within the scope of the present invention. The bottom surface 52 is preferably flat, but may have other configurations. As noted below, the exact configuration of the surfaces 50,52 may also depend on the strain that is placed on them prior to and during insertion. The outer peripheral surface 56 is preferably continuous in that it has no discontinuities. That is, the outer peripheral surface 56 is smooth and has no sharp angles (e.g., 30, 45 or 90° angles). Since the distal section 40 is to be deformed prior to insertion into the blood vessel 140, any sharp angles tend to create stress points, potentially causing the distal section 40 to be bent/deflected beyond its ability to return to its original configuration. The distal section 40 has a thickness that increases from the front (or distal) end 58 to the rear (or proximal) end 60. In the embodiment illustrated in the figures, the thickness increases from 0.28 mm at the front end 58 to 0.30 mm at the rear end 60. However, other thicknesses and tapered shapes fall within the scope of the present invention.

Figure 4B:
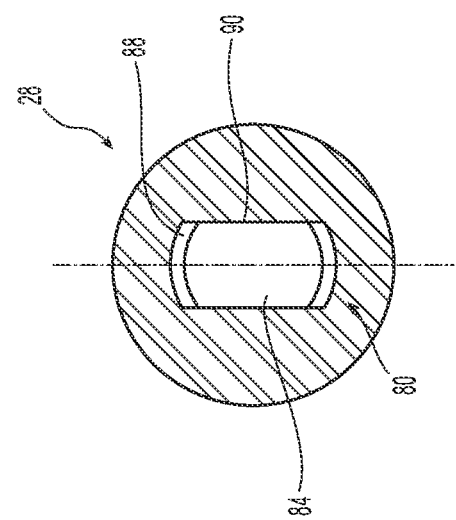
FIG. 4B is a cross section view of the second sealing element of the seal assembly of FIG. 2 that is orthogonal to the view in FIG. 2.
Figure 4A:
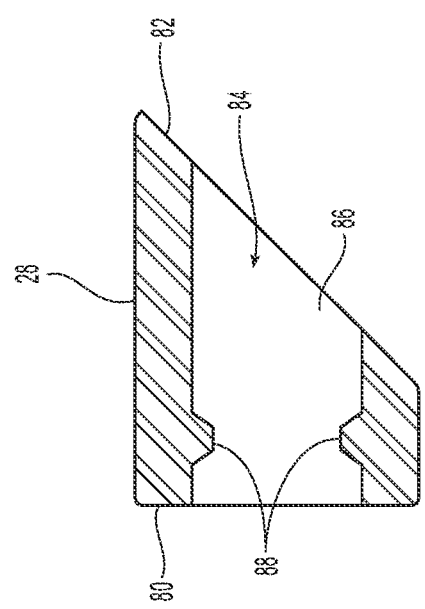
FIG. 4A is a cross section view along a longitudinal axis of a second sealing element of the seal assembly of FIG. 2.

Second sealing element 28 is shown in more detail in FIGS. 4A and 4B. The second sealing element 28 has a proximally facing surface 80 and a sloped distally facing surface 82. An internal opening 84 defined by the internal surface 86 extends between the proximally facing surface 80 and the sloped distally facing surface 82. The internal surface 86 has extending therefrom and into the internal opening 84 projections 88 that interface with and engage the knobs 62 with an interference fit such that second sealing element 28 and knobbed rigid shaft 24 function as a one way latch assuring an adequate compression force regardless of the blood vessel wall thickness.

The internal opening 84 of second sealing element 28 (and floating foot 26) have two flat surfaces 90 on opposite sides of the internal opening 84 that interface with flat surfaces 68,70 of knobbed rigid shaft 24 to provide rotational stability of the seal assembly components 26,28 thus assuring that the sloped distally facing surface 82 and the fully deployed floating foot 26 remain parallel with the distal section 40 of the first sealing element 22 and the proximal or top surface 50 in particular.

Figure 5A:
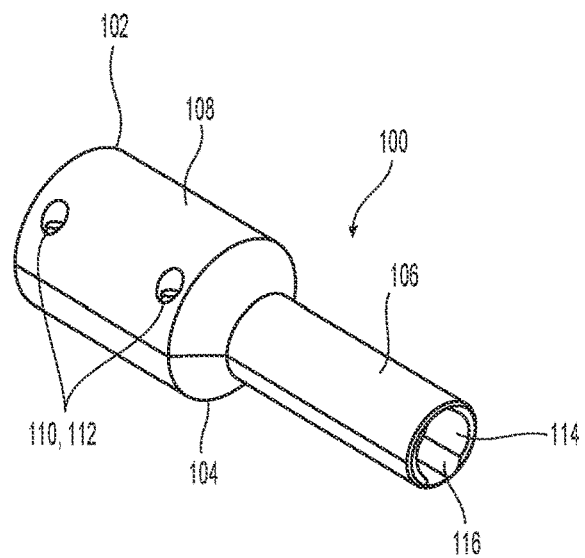
FIG. 5A is a perspective view of a sheath introducer used with the sealing device of FIG. 1.
Figure 5B:
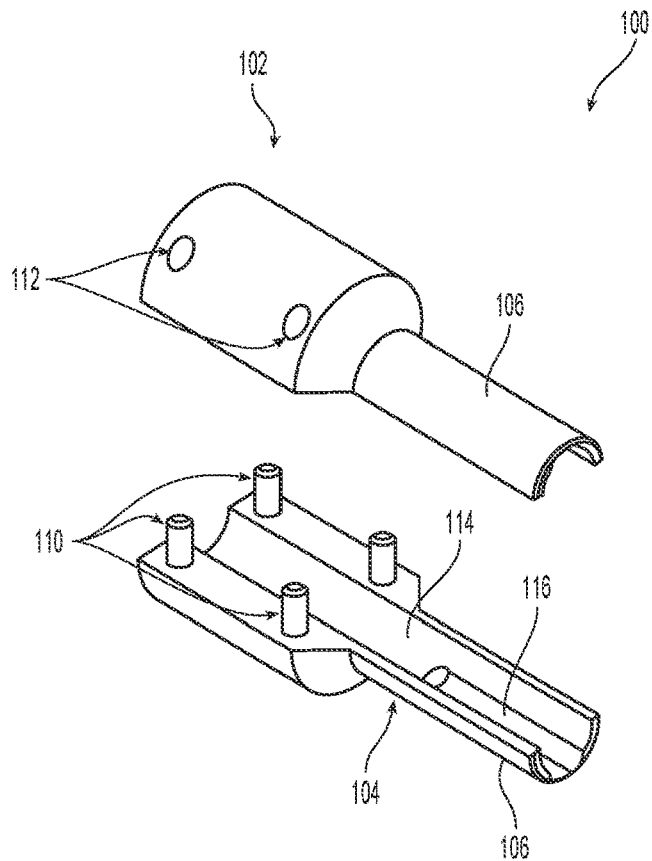
FIG. 5B is an exploded, perspective view of the sheath introducer of FIG. 5A.

FIGS. 5A and 6B depict introducer or outer sleeve 100, which is configured to protect seal assembly 20 from damage when inserting seal assembly 20 through a hemostatic valve, which, as discussed below and in more detail in the co-pending application, is one method in which the seal assembly is inserted into the patient. Introducer 100 comprises two halves, 102,104, which when assembled together form a generally cylindrical body having two different diameters. Front section 106 of introducer 100 has a smaller diameter than rear section 108. Front section 106 with the smaller diameter is configured to be inserted into hemostatic valve and rear section 108, having the larger diameter remains proximal to the hemostatic valve. While the two halves 102,104 can be assembled according to any typical manner, pins 110 on one of the two halves 102,104 are configured with a press fit into corresponding mating holes 112 thus holding halves 102,104 firmly together.

Figure 6:
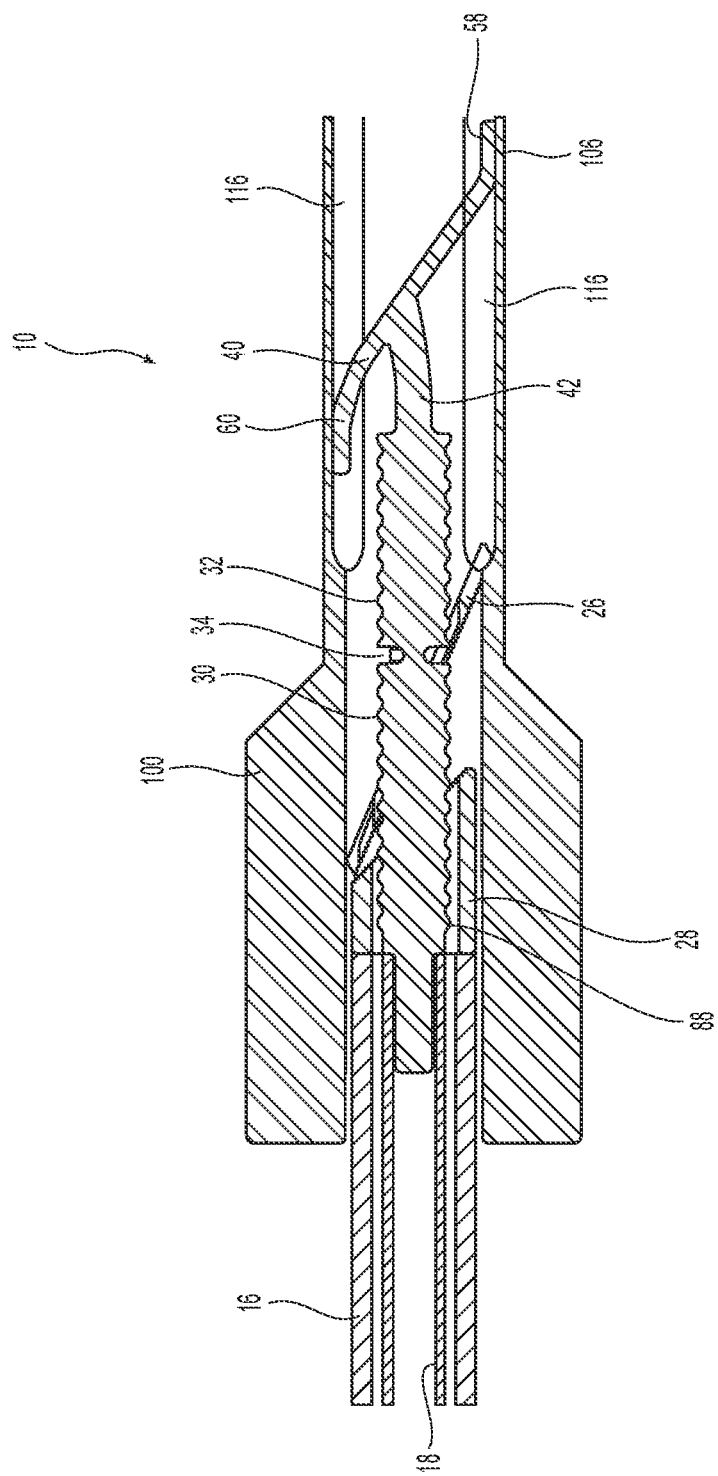
FIG. 6 is a cross section view of the seal assembly constrained in a sheath introducer.
Figure 10:
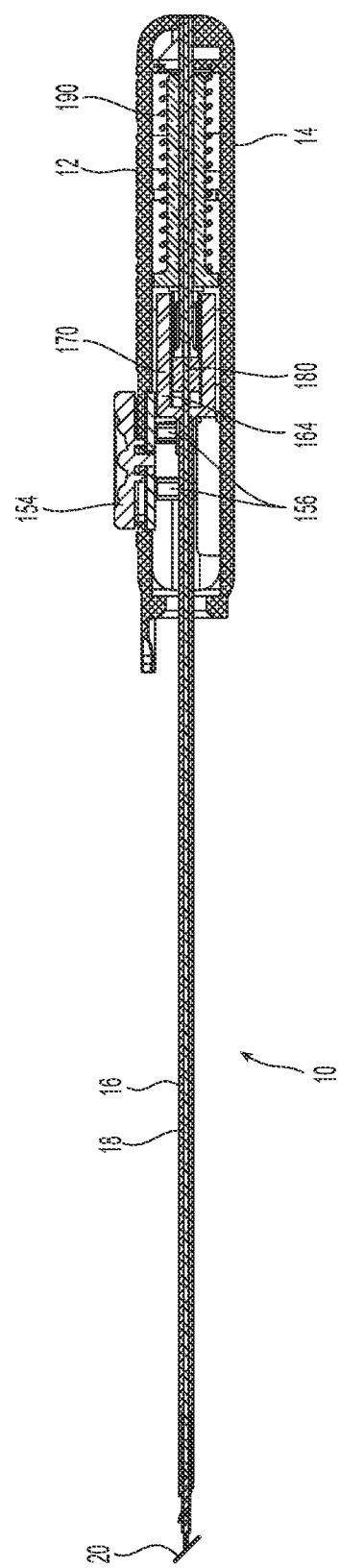
FIG. 10 is a cross section view of the sealing device of FIG. 1 along the longitudinal axis.
Figure 11:
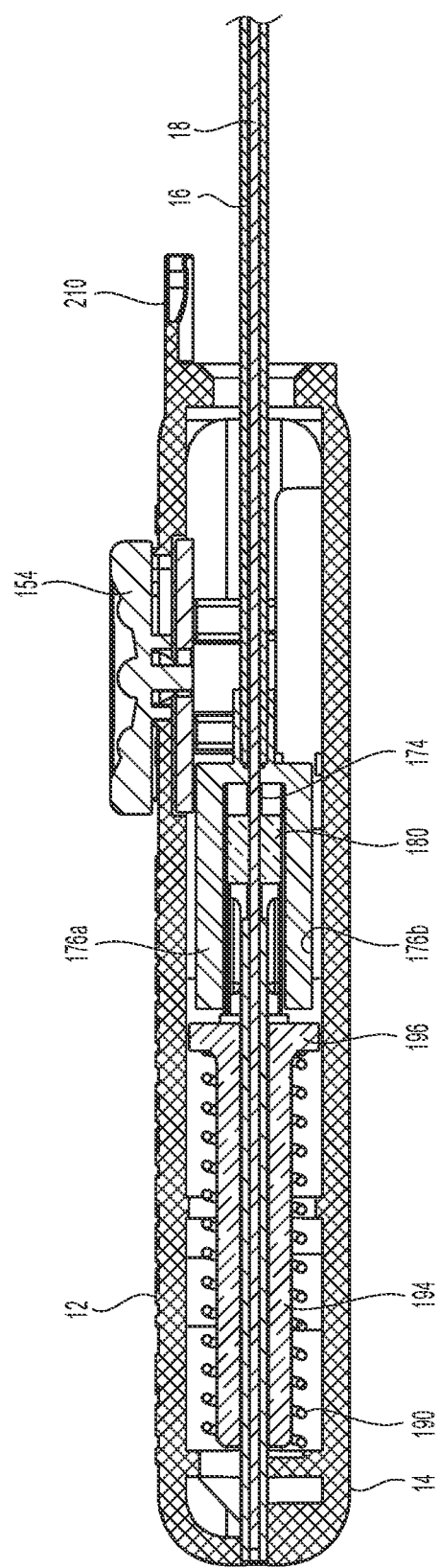
FIG. 11 is an enlarged, partial cross section view of the sealing device of FIG. 1.

The introducer 100 has an opening 114 that extends between the front section 106 and the rear section 108. However, within the opening 114 are also grooves 116 that are configured to accept seal assembly 20. The opening 114 is also configured to receive at least a portion of pusher 16 of the seal device 10. FIG. 6 is a cross section of seal assembly 20 in the initial position inside introducer 100 prior to insertion into a sheath 120. See FIG. 6. The front end 58 and the rear end 60 of the distal portion 40 of first sealing element 22 are deformed into a configuration such that the distal portion 40 of first sealing element 22 is able to pass through the inside dimension of cannula 122 upon insertion of closure device 10 resulting in the configuration shown in FIG. 6. After exit from distal end of cannula 122, the front end 58 and the rear end 60 of the distal portion 40 of first sealing element 22 return to the initial configuration as shown in FIG. 2 owing to the configuration shown in FIG. 6 not exceeding the elastic limit of the material from which the seal assembly 20 is constructed.

Turning now to the main portion of the closure device 10 and referring to FIGS. 7-13, closure device 10 comprises two handle halves 12, 14 that housing automatic mechanism 150. The automatic mechanism 150 interfaces with safety latch 152, which has a safety slide 154 that interacts with safety cage 156 via pin 158. The safety latch 152 operates such that with safety slide 154 in the distal most position automatic mechanism 150 cannot be activated. The proximal most position of safety slide 154 allows automatic activation, explained in more detail below. The pin 158 is in the center of the underside of safety slide 154 and passes through handle opening 160 of handle half 12 and engages slot 162 of safety cage 156. With the safety slide 154 in the full distal position, the pin 158 forces safety cage 156 into the position shown in FIG. 7 (to the left looking distally) such that leg 164 is forced into a slot 166 in pusher 170 that locks the movable pusher 170 against distal movement. The movement of the other parts of the automatic mechanism 150 are discussed in more detail below. In this position, safety slide 154 covers the word "READY" (or any other word, mark or appropriate indicia) and exposes the word "SAFE" (or any other word, mark or appropriate indicia) embossed on handle half 12. In this position, the safety latch 152 prevents the automatic mechanism 150 from premature firing during shipment or handling. With safety slide 154 in the proximal-most position, the pin 158 forces safety slide 154 to the right, thus removing leg 164 from the slot 166 in pusher 170. In this position the automatic mechanism 150 is free to initiate when first sealing element 22 interacts with the inside of vessel wall 142. In this configuration safety slide 154 covers the word "SAFE" and exposes the word "READY" on handle half 12.

Flexible pusher rod 16 is a cannulated cylinder, the proximal end of which is connected by an adhesive or by another appropriate method to the movable pusher 170. The movable pusher 170 has a front portion 172 with an opening 174 for engagement with the flexible pusher rod 16 and to allow the flexible shaft 18 to pass through front portion 172. The pusher 170 also has a rear portion 176 that is divided into an upper portion 176a and a lower portion 176b, the upper portion 176a and a lower portion 176b defining an opening 178 therebetween.

The automatic mechanism 150 also includes a shaft retaining element 180 that, in the initial or preactivation stage, is disposed in opening 178 defined by the upper portion 176a and a lower portion 176b of pusher 170. The shaft retaining element 180 also has an opening 182 passing therethrough to allow the flexible shaft 18 to pass therethrough and extend proximally in the automatic mechanism 150. However, the flexible shaft 18 is fixedly attached to the shaft retaining element 180. The flexible shaft 18 therefore extends almost the entire length of the device 10. As noted above, the flexible shaft 18 is also connected to the knobbed rigid shaft 24 of the seal assembly 20. As explained below, a tensile force on the flexible shaft 18 causes the automatic mechanism 150 to fire.

The automatic mechanism 150 also has a spring 190, which is illustrated as a cylindrical spring, but could be any resilient element and have any configuration. The spring 190 engages, at its proximal end, the proximal end of the handle 12,14. The spring 190 is disposed around a spring retainer 194 and engages at its distal end, the front end 196 of the spring retainer 194. The spring 190 is biased against the front end 196 of the spring retainer 194 to push the spring retainer 194 against the pusher 170, as described in more detail below.

The automatic mechanism 150 also has two retention elements 200 that are rotatably mounted in the housing 12,14. The two retention elements 200 are illustrated as being generally triangular, but could be of any shape or configuration as long as they perform the functions noted below. The retention elements 200 are disposed to engage the front end 196 of the spring retainer 194 and the shaft retaining element 180. In fact, each of the two retention elements 200 engage a notch 202 on either side of the shaft retaining element 180. The retention elements 200 each have an end portion 204, preferably a flat surface, that engages an internal surface of the notches 202. As can best be seen in FIG. 9, the retention elements 200 are disposed on round projections 206 extending upward from the handle 14. The projections 206 could also project downward from the handle 12.

Figure 12:
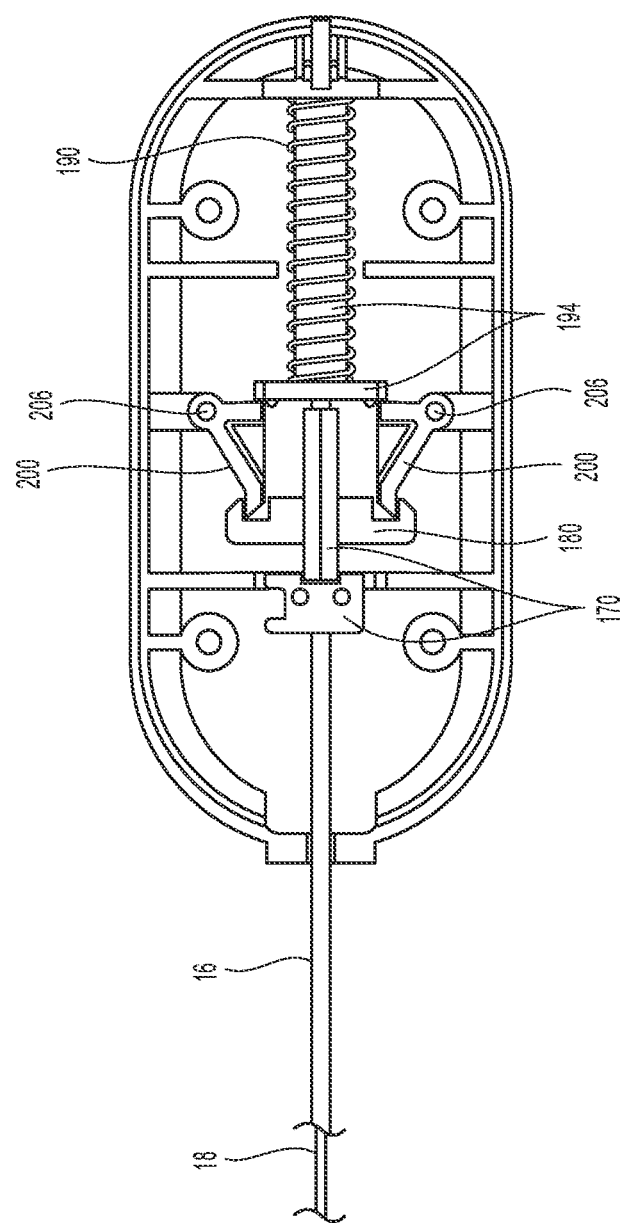
FIG. 12 is a top view of the sealing device of FIG. 1 with the top half of the handle and safety latch removed in a pre-insertion configuration.
Figure 13:
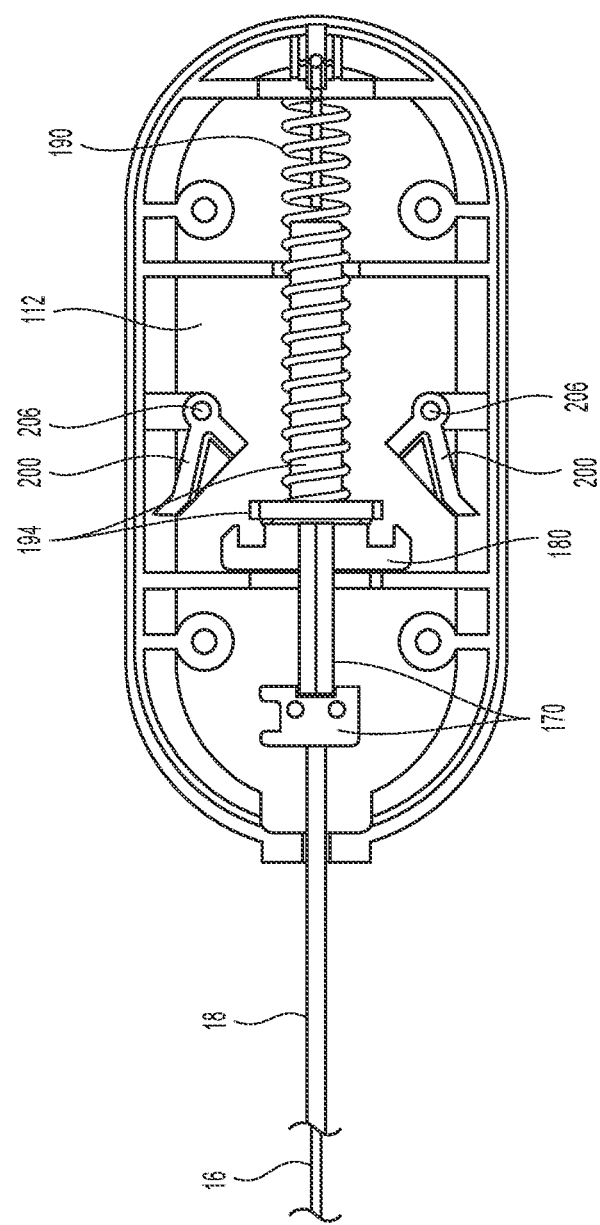
FIG. 13 is a top view of the sealing device of FIG. 1 with the top half of the handle and safety latch removed in a post-firing configuration.
Figure 14:
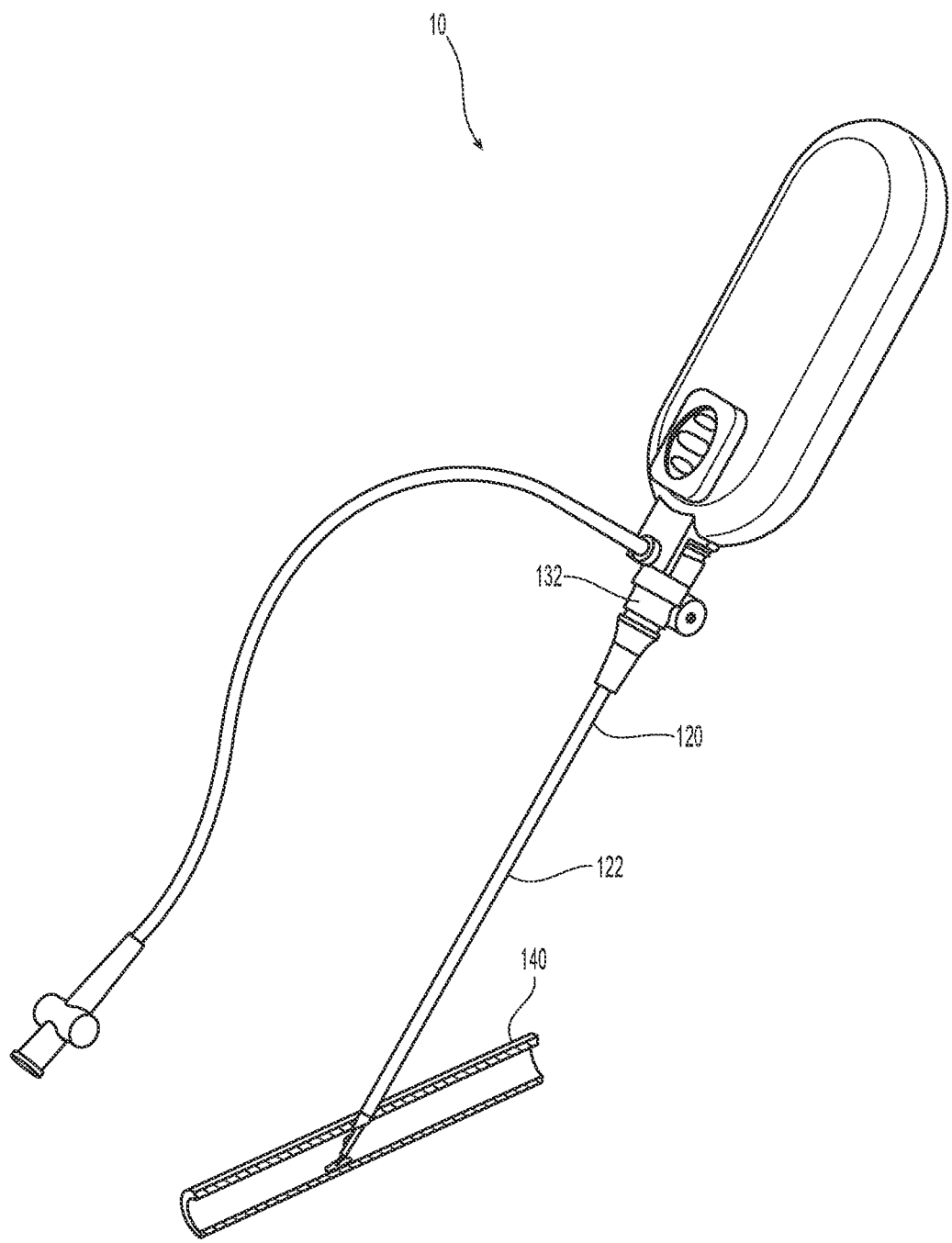
FIG. 14 is a perspective view of the sealing device inserted into a blood vessel.

The use of the device 10 will now be described in conjunction with FIGS. 12-17. FIGS. 12 and 13 are top views of the device with the upper handle half 12 and the safety latch 152 removed for clarity and to show pre-firing and post-firing, respectively. In FIG. 12, the spring 190 is compressed by spring retainer 194, which when released will provide the kinetic energy to seal the opening in the blood vessel and to break the knobbed rigid shaft 24. The spring retainer 194, and in particular the front end 196, is biased against the retention elements 200. The retention elements 200 cannot move due to the end portion 204 engaging the internal surface of the notches 202 of the shaft retaining element 180. The front end 196 of spring retainer 194 is separated from the pusher 170 by the retention elements 200. Keeping in mind that the shaft retaining element 180 is secured to the flexible shaft 18, which in turn is secured to the knobbed rigid shaft 24, pulling on the seal assembly 20 will cause the flexible shaft 18 to be pulled distally and move shaft retaining element 180 distally as well. This allows the retention elements 200 to rotate outward given the biasing of the front end 196 of the spring retainer 194. The front end 196 of the spring retainer 194 can then push pusher 170 connected to the flexible pusher rod 16 distally. The effect of this movement is illustrated in FIG. 13.

Figure 17:
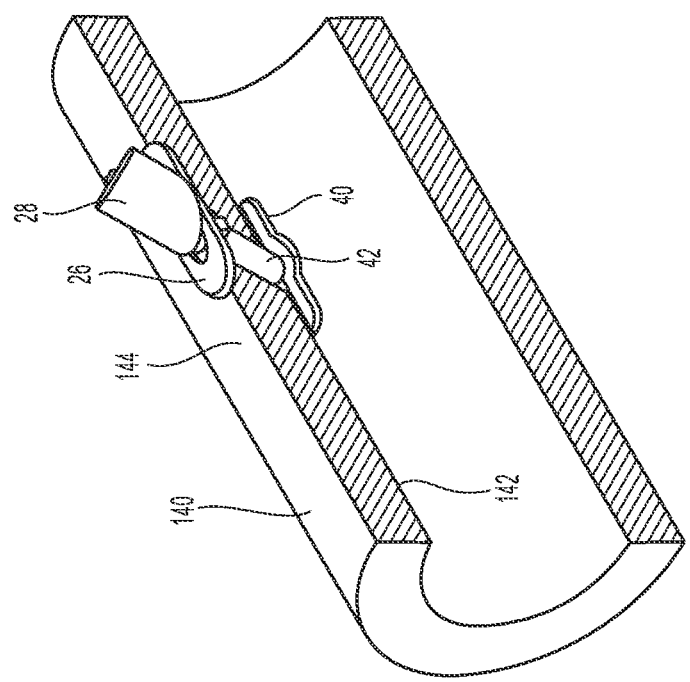
FIG. 17 is a perspective view of the seal assembly blocking the opening in the blood vessel after activation of the sealing device.
Figure 18:
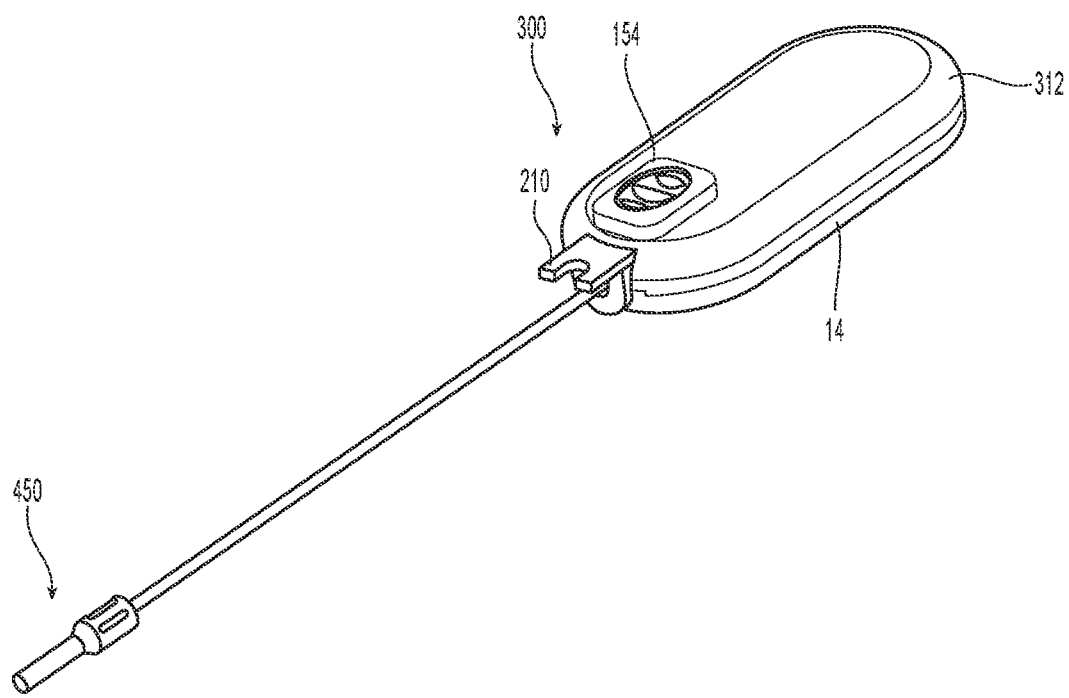
FIG. 18 is a perspective view of another embodiment of a sealing device according to the present invention.

A method of using the current invention in conjunction with FIGS. 14-17 is as follows: The device 10, and in particular the seal assembly 20 is inserted into sheath introducer 100 that surrounds and deforms seal assembly 20 such that seal assembly seal 20 can pass through sheath valve 132. See also FIG. 6. The device 10 and sheath introducer 100 is inserted into a hemostatic valve for insertion into the patient. The device 10 preferably has a latch 210 that can be used to attach the device 10 to the sheath 120. This allows for the simultaneous removal of the device 10 and the sheath 120, if the sheath is not removed prior to the activation of the automatic mechanism 150. Inserting pusher 16 through sheath 120, including valve 132 and cannula 122, causes at least a portion of seal assembly 20 to exit the distal end of cannula 122 and into blood vessel 140. See FIG. 14. A portion of the second sealing element 28 and the pusher 16 may be disposed within the blood vessel 140. See FIG. 15. The sheath 120 may then be removed from the device 10. Pulling on the closure device 10, the proximal or top surface 50 of the distal portion 40 of first sealing element 22 engages the interior blood vessel wall 142. See FIG. 16. This would also remove the second sealing element 28, the outer floating element 26, and the pusher 16 from within the blood vessel 140. Continuing to pull on the sealing assembly 20 and therefore flexible shaft 18 triggers the automatic mechanism 150 in the closure device 10, which pushes pusher 16, and which in turn pushes second sealing element 28, and floating foot 26 distally such that floating foot 26 is in contact with outer wall of blood vessel 140. This will sandwich the second sealing element 28 against floating foot 26, blood vessel 140 and distal portion 40 of first sealing element 22 such that the opening in blood vessel 140 is hemostatically sealed, as shown in FIG. 17.

The initial spring compression is chosen such that accounting for friction losses the remaining kinetic energy is sufficient to break weakened notch feature 34 of knobbed rigid shaft 24 resulting in the distal truncated portion of seal assembly 20 becoming detached from the rest of closure device 10 and also providing vessel hemostasis as shown in FIG. 17. Note that as the user moves sheath 120 and closure device 10 proximally activating the automatic process and removes the two latched components, the handle and the sheath, from the body nothing remains in the patient except the bio-absorbable truncated portion of seal assembly 20. Thus the entire closure process of sealing and disconnection is automatic requiring no "tactical feel" of the user.

Turning to another embodiment, a closure device 300 is illustrated in FIGS. 18-35, comprises two handle halves 312, 314 housing an automatic mechanism.

Figure 19:
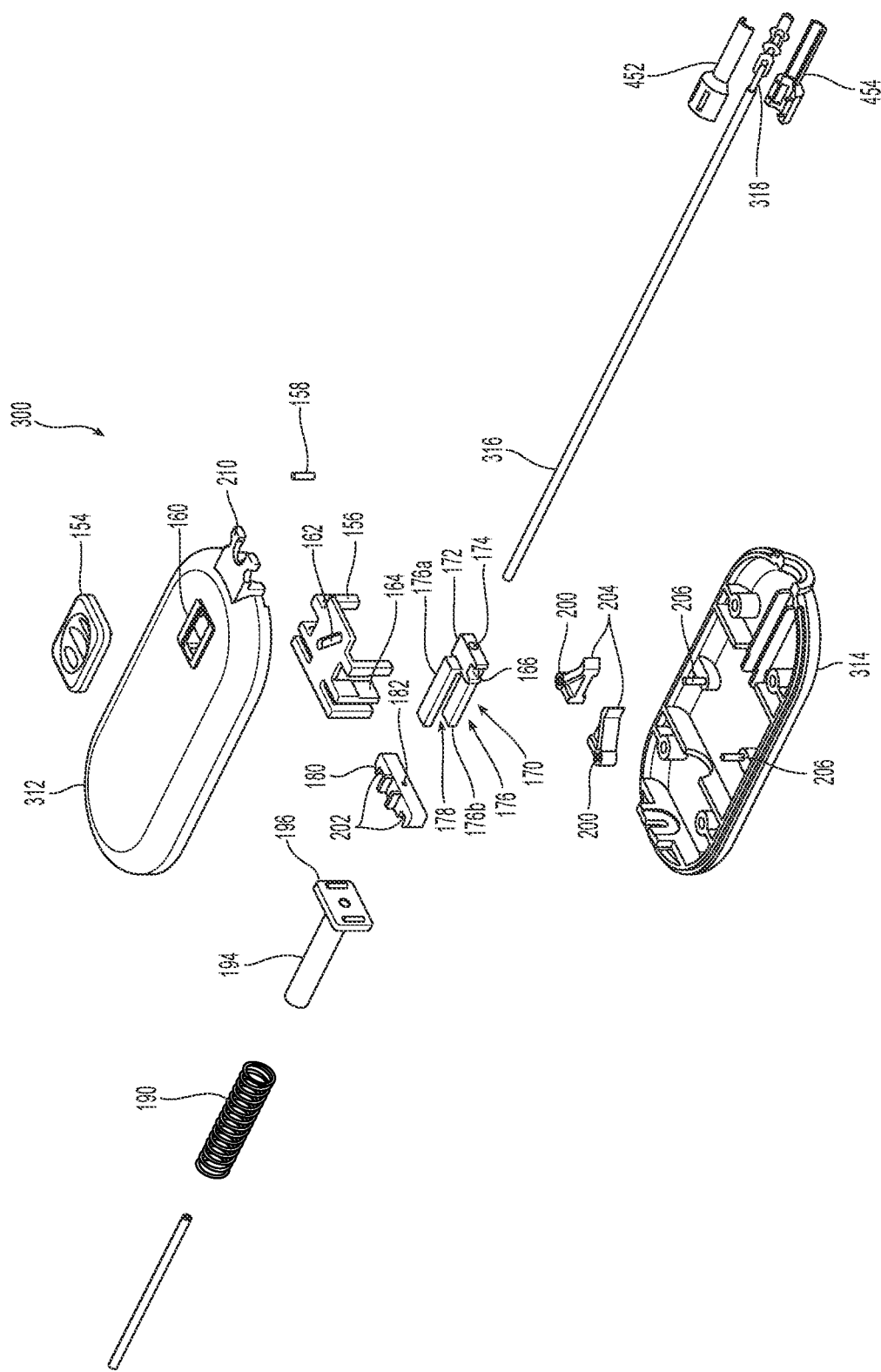
FIG. 19 is a perspective view of a portion of the sealing device of FIG. 18 illustrating the seal assembly thereof.

More specifically and referring to FIG. 19, closure device 300 comprises two handle halves 312,314 that housing automatic mechanism 150. The automatic mechanism 150 interfaces with safety latch 152, which has a safety slide 154 that interacts with safety cage 156 via pin 158. The safety latch 152 operates such that with safety slide 154 in the distal most position automatic mechanism 150 cannot be activated. The proximal most position of safety slide 154 allows automatic activation. The pin 158 is in the center of the underside of safety slide 154 and passes through handle opening 160 of handle half 312 and engages slot 162 of safety cage 156. With the safety slide 154 in the full distal position, the pin 158 forces safety cage 156 such that leg 164 is forced into a slot 166 in pusher 170 that locks the movable pusher 170 against distal movement. In this position, safety slide 154 covers the word "READY" (or any other word, mark or appropriate indicia) and exposes the word "SAFE" (or any other word, mark or appropriate indicia) embossed on handle half 312. In this position, the safety latch 152 prevents the automatic mechanism 150 from premature firing during shipment or handling. With safety slide 154 in the proximal-most position, the pin 158 forces safety slide 154 to the right, thus removing leg 164 from the slot 166 in pusher 170. In this position the automatic mechanism 150 is free to initiate when first sealing element 320 interacts with the inside of a vessel wall. In this configuration safety slide 154 covers the word "SAFE" and exposes the word "READY" on handle half 312.

Flexible pusher rod 316 is a cannulated cylinder, the proximal end of which is connected by an adhesive or by another appropriate method to the movable pusher 170. The movable pusher 170 has a front portion 172 with an opening 174 for engagement with the flexible pusher rod 16 and to allow the flexible shaft 218 to pass through front portion 172. The pusher 170 also has a rear portion 176 that is divided into an upper portion 176a and a lower portion 176b, the upper portion 176a and a lower portion 176b defining an opening 178 therebetween.

The automatic mechanism 150 also includes a shaft retaining element 180 that, in the initial or preactivation stage, is disposed in opening 178 defined by the upper portion 176a and a lower portion 176b of pusher 170. The shaft retaining element 180 also has an opening 182 passing therethrough to allow the flexible shaft 318 to pass therethrough and extend proximally in the automatic mechanism 150. However, the flexible shaft 318 is fixedly attached to the shaft retaining element 180. The flexible shaft 318 therefore extends almost the entire length of the device 300. As noted above, the flexible shaft 318 is also connected to the knobbed rigid shaft 326 of the seal assembly 320. A tensile force on the flexible shaft 318 causes the automatic mechanism 150 to fire.

The automatic mechanism 150 also has a spring 190, which is illustrated as a cylindrical spring, but could be any resilient element and have any configuration. The spring 190 engages, at its proximal end, the proximal end of the handle 312,314. The spring 190 is disposed around a spring retainer 194 and engages at its distal end, the front end 196 of the spring retainer 194. The spring 190 is biased against the front end 196 of the spring retainer 194 to push the spring retainer 194 against the pusher 170, as described in more detail below.

The automatic mechanism 150 also has two retention elements 200 that are rotatably mounted in the housing 312,314. The two retention elements 200 are illustrated as being generally triangular but could be of any shape or configuration as long as they perform the functions noted below. The retention elements 200 are disposed to engage the front end 196 of the spring retainer 194 and the shaft retaining element 180. In fact, each of the two retention elements 200 engage a notch 202 on either side of the shaft retaining element 180. The retention elements 200 each have an end portion 204, preferably a flat surface, that engages an internal surface of the notches 202. The retention elements 200 are disposed on round projections 206 extending upward from the handle 314. The projections 206 could also project downward from the handle 312.

The automatic mechanism is coupled to the seal assembly 320 by a flexible pusher 316 and a flexible shaft 318, as in the prior embodiment. Seal assembly 320 has a first sealing element 322, a flexible member 324, a knobbed rigid shaft 326, an outer floating element 328, and a second sealing element 330. Knobbed, rigid shaft 326 has a proximal section 332 and a distal section 334 separated by a weakened notch feature 336, which is configured to separate seal assembly 320 from the rest of the closure device 300 once the automatic deployment and sealing process is complete. The length of the distal section 334 of knobbed shaft 326 is dictated by the thickness of the vessel wall that can be accommodated. The first sealing element 322 also has a distal section 340 configured to, with the assistance of the flexible member 324, interface with the inside wall of a vessel to be sealed; a knobbed, rigid distal shaft section 334 (which is a part of the knobbed, rigid shaft 326); and ankle section 342 joining the distal section 340 to the knobbed, rigid distal shaft section 334. The ankle section 342 is attached to distal section 340 at an angle α, which is preferably at an angle of about 45°. See FIG. 22. Although other angles may be used, the value of angle α may cause other values of the seal assembly to be changed. Applicant also notes the that the first sealing element 322 is formed with the distal section 340, ankle section 342, and the knobbed, rigid shaft 326 at the same time and from the same material. As such, the first sealing element 322 is an integrally formed element and the distal section 340 is not designed to move relative to the knobbed, rigid distal shaft section 334 at any time, except through deformity. As indicated in the parent patent, the first sealing element is preferably a one single-piece component.

Figure 20A:
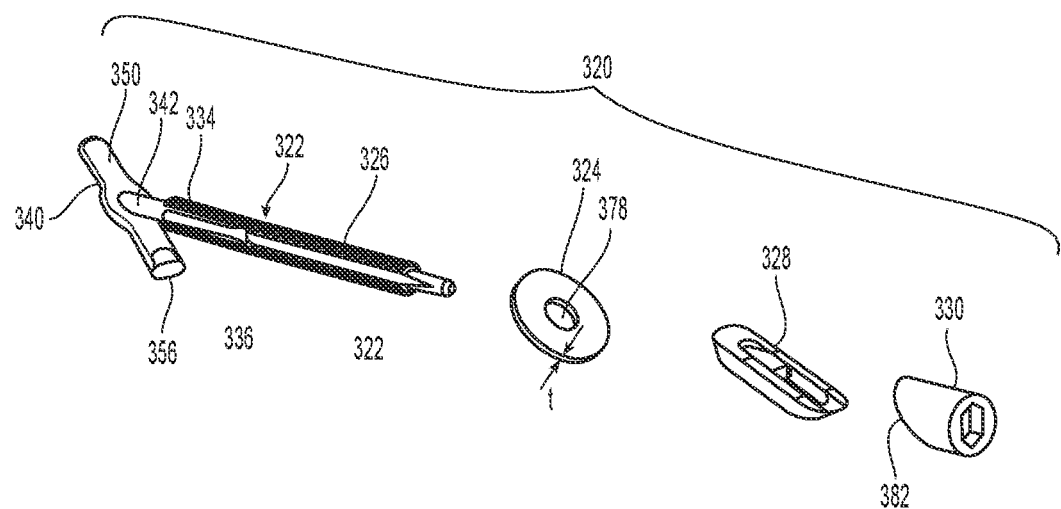
FIG. 20A is an exploded, perspective view of the first sealing element and the shaft.
Figure 20B:
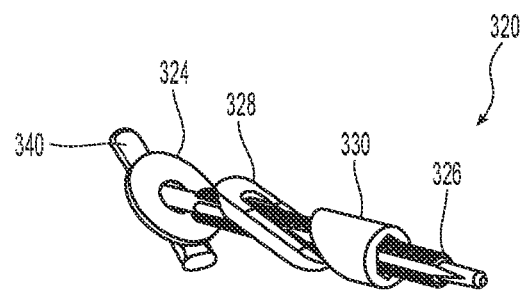
FIG. 20B is a perspective view of the first sealing element and the shaft of FIG. 20A in an assembled state.
Figure 20C:
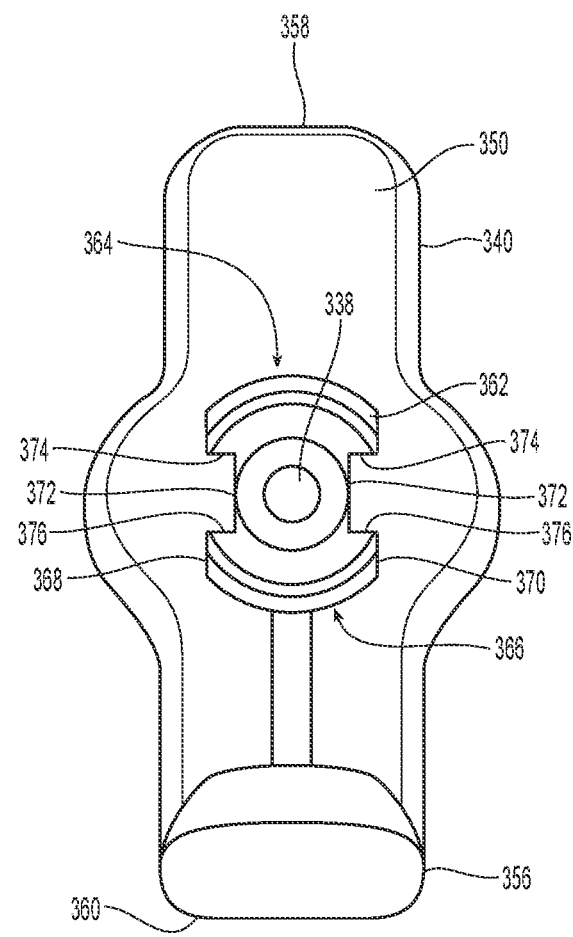
FIG. 20C is a top view of the first sealing element and shaft looking down the shaft.
Figure 21:
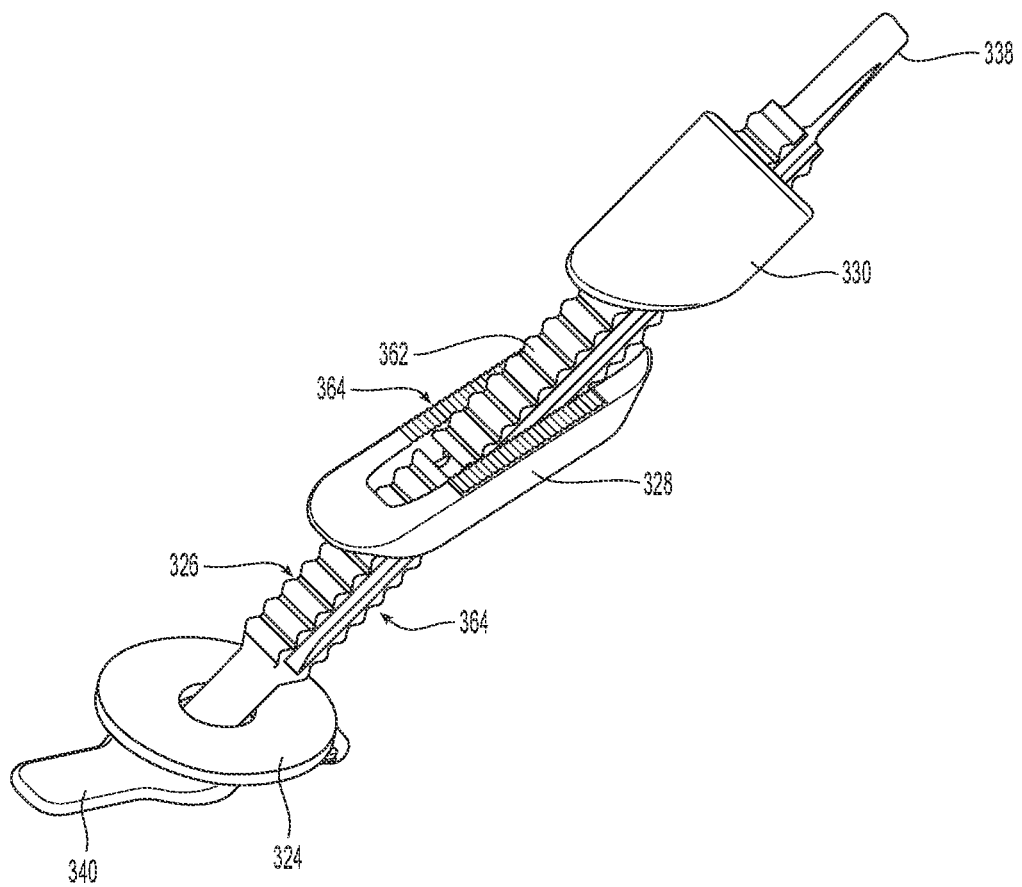
FIG. 21 is a perspective view of the seal assembly of FIG. 19.
Figure 22:
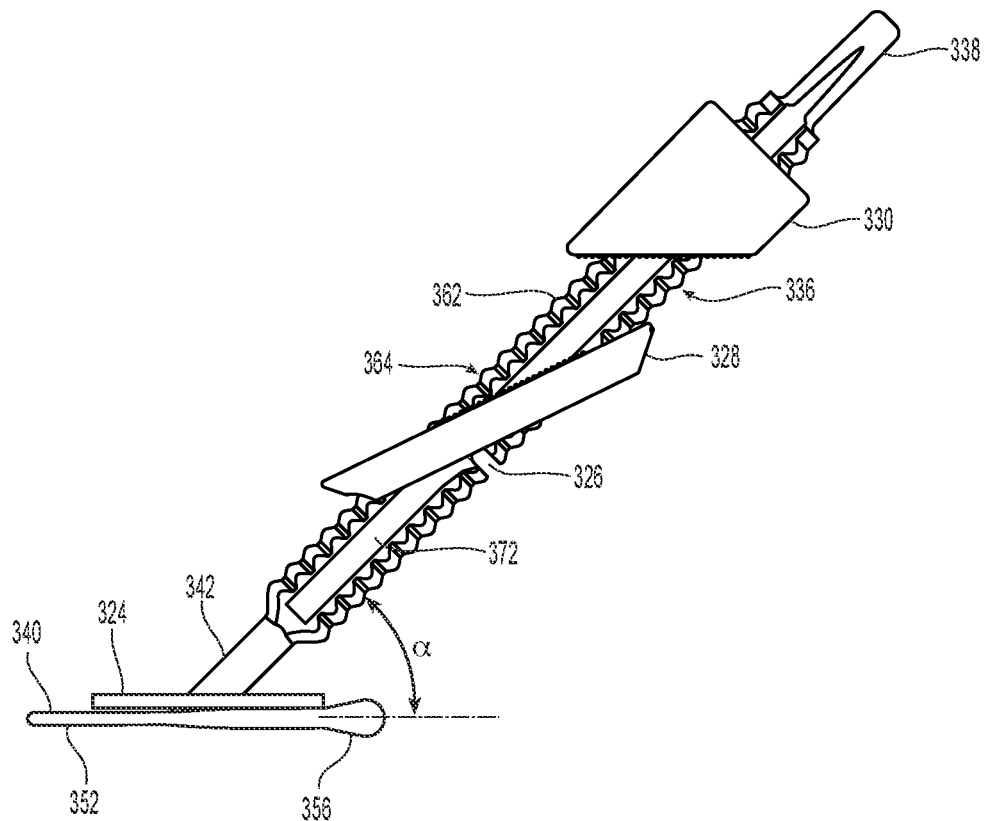
FIG. 22 is a side view of the of the seal assembly of FIG. 19.
Figure 23:
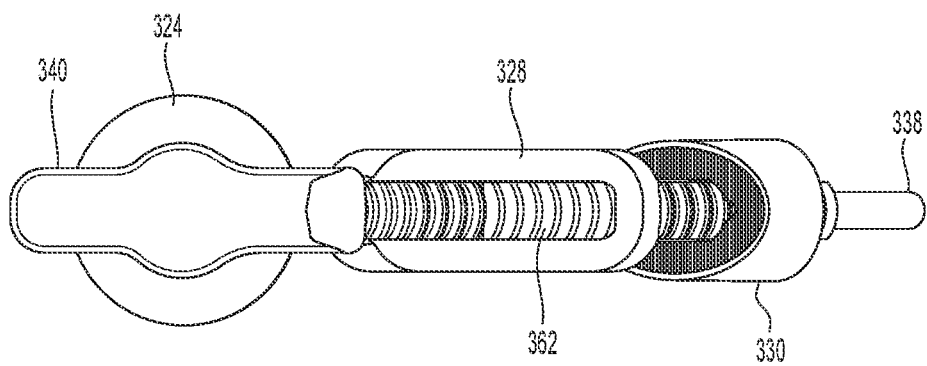
FIG. 23 is a bottom view of the of the seal assembly of FIG. 19.

A more detailed view of the first sealing element 322 and the knobbed rigid shaft 326 is presented in FIGS. 20A-21. The first sealing element 322 has the distal section 340, ankle section 342 and the knobbed, rigid distal shaft section 334. The distal section 340 has a proximal or top surface 350, a bottom surface 352 and a heel 356. The top surface 350 can be of any configuration (e.g., flat, convex, etc) and still come within the scope of the present invention. The bottom surface 352 is preferably flat, but may have other configurations as well. The heel 356 preferably has a greater thickness than the remainder of the distal section 340 and, as discussed below is disposed into a cavity in the inserter. The distal section 340 has a thickness that increases from the front (or distal) end 358 to the rear (or proximal) end 360. In the embodiment illustrated in the figures, the thickness increases from 0.28 mm at the front end 358 to 0.30 mm at the rear end 360. However, other thicknesses and tapered shapes fall within the scope of the present invention.

A top view of the knobbed, rigid shaft 326 and the first sealing element 322 is illustrated in FIG. 20C. The knobbed, rigid shaft 326 has a proximal end 338 that may be connected to the flexible shaft 318 in any appropriate fashion, e.g., glued, soldered, press-fit, friction fit, etc. Alternatively, the flexible shaft 318 may also be integral with the knobbed, rigid shaft 326, i.e., be formed at the same time with the same material making it an "integral" piece. The knobbed, rigid shaft 326 has knobs 362 along the upper surface 364 and the lower surface 366. The knobbed, rigid shaft 326 also has opposite sides 368,370, each side of which includes a groove 372 that runs along the length of the knobbed, rigid shaft 326 between the ankle section 342 and the proximal end 338. The grooves 372 are preferably rectangular (or square) in cross section for reasons that will become apparent below. As such each of the grooves 372 have a front (or first) surface 374 and a rear (or second) surface 376. It is noted that the front surface 374 faces the rear portion of the knobbed, rigid shaft 326, while the rear surface 376 faces the front of the knobbed, rigid shaft 326. The grooves 372 cooperate with the other portions of the seal assembly 320 to ensure that the outer floating element 328 and the second sealing element 330 are properly positioned, as discussed in more detail below. Since the grooves 372 are smaller than the sides 368,370, the sides 368,370 present a flat surface for the outer floating element 328, discussed below.

Figure 24:
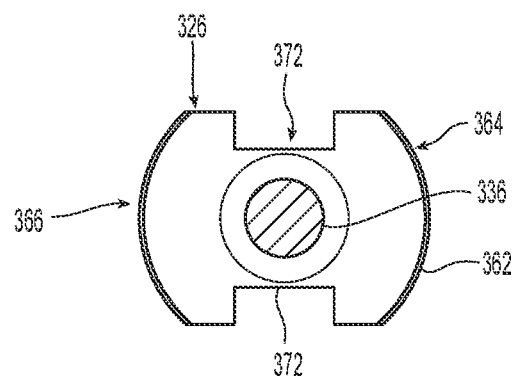
FIG. 24 is a cross section view of the shaft at the location of the reduced portion.
Figure 25:
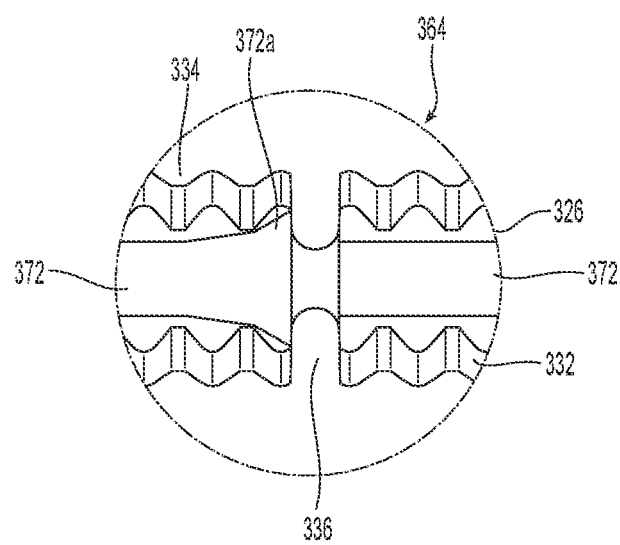
FIG. 25 is a partial side view of the shaft at the location of the reduced portion.

Illustrated in FIGS. 24 and 25 is a cross section of the knobbed, rigid shaft 326 at the weakened notch feature 336. The weakened notch feature 336 has a smaller cross section than any other portion of the knobbed rigid shaft 326. This allows for the knobbed, rigid shaft 326 to be broken at this point upon activation of the insertion device 300 by exerting a force in the direction of the length of the knobbed, rigid shaft 326, causing the knobbed, rigid shaft 326 to break at the weakened notch feature 336. In order to prevent the weakened notch feature 336 from breaking prematurely, a c-shaped ring may be clipped into the weakened notch feature 336 as noted above. The width of notch feature 336 is sized to equal the space between knobs 362 so that second seal 328 can easily transition over notch feature 336 upon automatic activation of device 300. The c-shaped ring prevents the knobbed, rigid shaft 326 from being tilted off center and breaking prematurely.

In FIG. 25, the groove 372 in the knobbed, rigid distal shaft section 334 preferably flares outward at 372a at the weakened notch feature 336, to ensure that the outer floating element 328 and its components float over the weakened notch feature 336 during operation without skiving on a portion of the groove 372 at that location.

The flexible member 324, along with distal section 340, assists in sealing the opening in the vessel wall. The flexible member 324 is illustrated as being a circular member having an opening 378 in a middle portion thereof. The flexible member 324 has a thickness t, which is preferably around 0.2 millimeters. Since the flexible member 324 is preferably made from 70% L-lactide 30% caprolactone copolymer, it is able to being deformed as described below. As illustrated in FIGS. 20B and 21, the flexible member 324 is disposed around the ankle portion 342 and against the top surface 350 of the distal section 340. Preferably, the flexible member 324 is attached to the top surface 350 of the distal section 340. It can be attached in any number of ways, including heat-staking or welding the flexible member 324 to the top surface 350, using an approved adhesive between the flexible member 324 and the top surface 350 flexible member 324. Alternatively, the opening 378 could be slightly smaller than the diameter of the ankle portion 342, preventing the flexible member 324 from moving along the length of the knobbed, rigid shaft 326 at the ankle portion 342. As explained in more detail below, the flexible member 324 is disposed between the distal section 340 and the inner wall of the vessel. See, e.g., FIG. 34.

While the opening 378 is a contained opening, it is also possible that there be a slit (or small path) from the outside of the flexible member 324 allowing the flexible member to be disposed around the ankle portion 342 without having to slide it the length of the knobbed, rigid shaft 326.

Figure 26A:
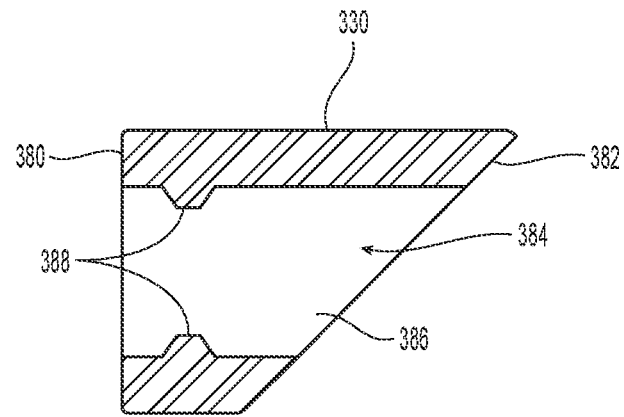
FIG. 26A is a cross section view along a longitudinal axis of a second sealing element of the seal assembly of FIG. 20.
Figure 26B:
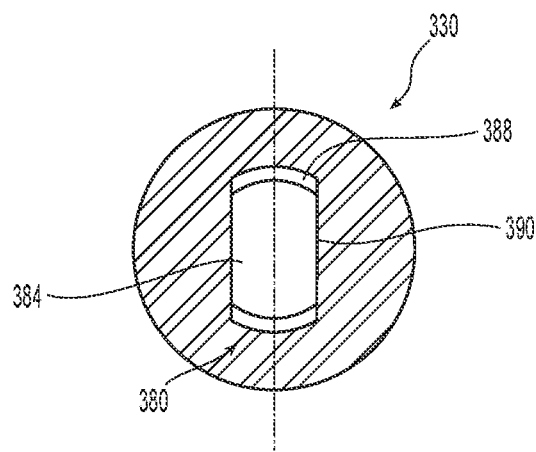
FIG. 26B is a cross section view of the second sealing element of the seal assembly of FIG. 20 that is orthogonal to the view in FIG. 26A.
Figure 27A:
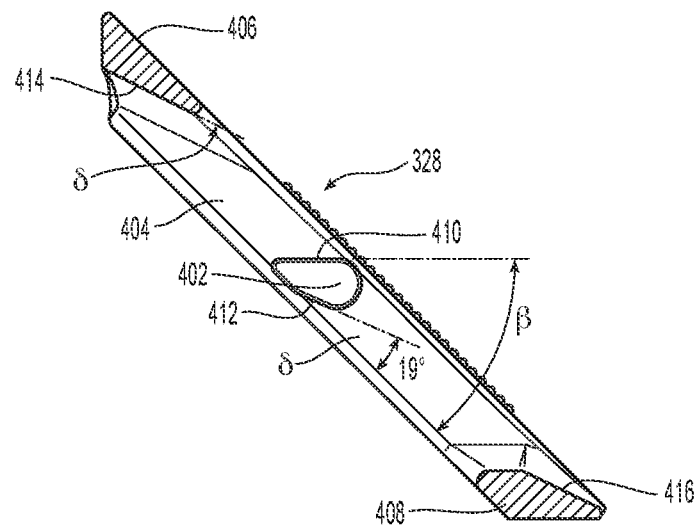
FIG. 27A is a side view of a cross section of another embodiment of an outer floating member.
Figure 27B:
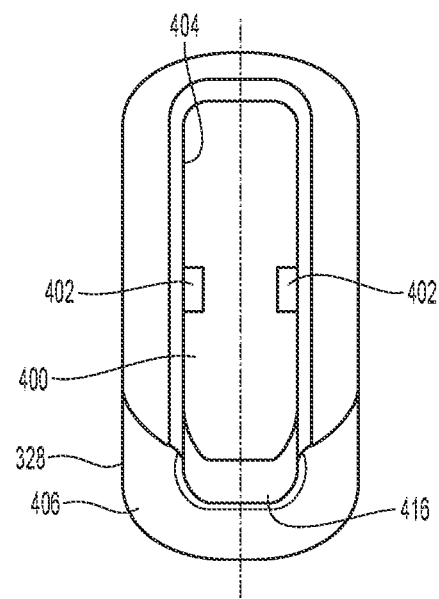
FIG. 27B is a top view of the outer floating member of FIG. 26A.

Second sealing element 330 is shown in more detail in FIGS. 26A and 26B and is the same as that illustrated in FIGS. 4A and 4B. The second sealing element 330 has a proximally facing surface 380 and a sloped distally facing surface 382. An internal opening 384 defined by the internal surface 386 extends between the proximally facing surface 380 and the sloped distally facing surface 382. The internal surface 386 has extending therefrom and into the internal opening 384 projections 388 that interface with and engage the knobs 362 with an interference fit such that second sealing element 330 and knobbed, rigid shaft 326 function as a one way latch assuring an adequate compression force regardless of the blood vessel wall thickness.

Referring to FIG. 26B, the internal opening 384 of second sealing element 330 have two flat surfaces 390 on opposite sides of the internal opening 384 that interface with flat surfaces 368,370 of knobbed rigid shaft 326 to provide rotational stability of the seal assembly components 328, 330, thus assuring that the sloped distally facing surface 382 and the fully deployed outer floating foot 328 remain parallel with the distal section 340 of the first sealing element 322 and the proximal or top surface 350 in particular.

The outer floating element 328 is illustrated in detail in FIGS. 27A-28B. The outer floating element 328 is generally rectangularly shaped and has a rectangularly shaped central aperture 400 and two protrusions 402 that extend from the longest side walls 404 into the aperture 400. The outer floating element 328 has a top surface 406 and a bottom surface 408, which are generally parallel to one another. The protrusions 402 are configured to engage and allow the outer floating element 328 to travel along the knobbed, rigid shaft 326 in the grooves 372. The protrusions are somewhat tear drop shaped, but have two flat surfaces, a first flat surface 410 and a second flat surface 412. The outer floating element 328 also has two inclined surfaces 414 and 416, one at either end of the outer floating element 328 and defines the ends of the aperture 400. The first flat surface 410 is at an angle ß relative to the top and bottom surfaces 406,408 of outer floating element 328. See FIG. 23A. Preferably angle β is about a 45 degree angle but could be anywhere between 35 and 55 degrees and still fall within the scope of the present invention. The second flat surface 412 makes an angle γ relative to the top and bottom surfaces 406,408. See FIG. 27A. Preferably angle γ is about a 19 degree angle but could be anywhere between 15 and 25 degrees and still fall within the scope of the present invention. As would be obvious, the two inclined surfaces 414 and 416 are also parallel to the second flat surface 412 as will be explained below.

Figure 28A:
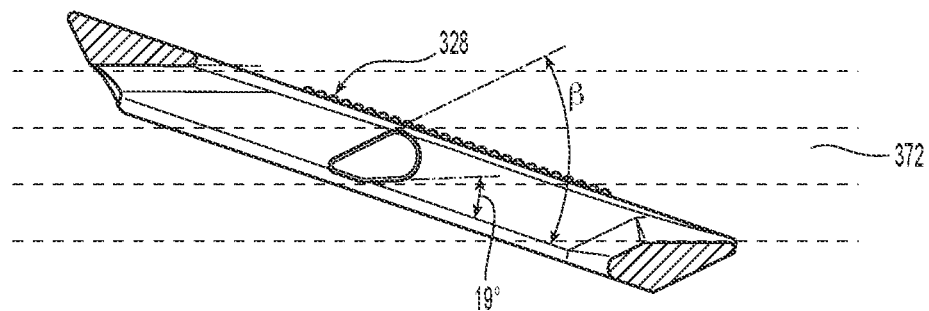
FIG. 28A is a side view of cross section view of the outer floating member in FIG. 22A in a first position relative to the shaft.
Figure 28B:
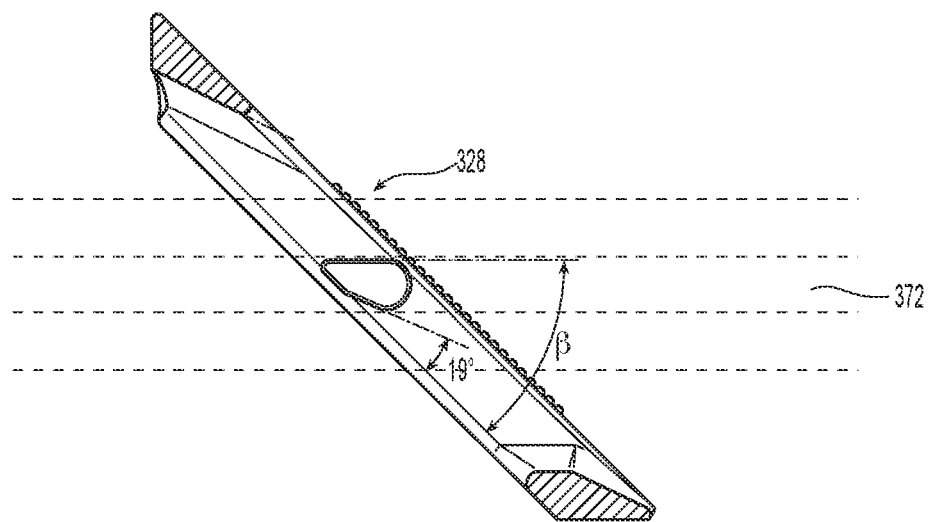
FIG. 28B is a side view of cross section view of the outer floating member in FIG. 26A in a second position relative to the shaft.

Turning to FIGS. 28A and 28B, the positioning of the outer floating element 328 will be explained. In both figures, the dotted lines correspond to the surfaces of the knobbed, rigid shaft 326 presented to the outer floating element 328. In particular, the two middle lines correspond to the front (or first) surface 374 and the rear (or second) surface 376 of the groove 372. Thus, the two protrusions 402 will slide along between those two middle lines. The two outside lines correspond to the upper 364 surface and the lower 366 surface of the outer floating element 328. In FIG. 28A, the outer floating element 328 is illustrated in its stored version—to be inserted into, or already in the inserter. Thus, in the position of FIG. 28A, the outer floating element 328 has, relative to the rest of the seal assembly 320, the smallest profile and will allow it to pass through a smaller cannula.

FIG. 28B illustrates the outer floating element 328 relative to the knobbed, rigid shaft 326 after it exits the cannula. That is, the outer floating element 328 has been engaged by the second sealing element 330 (not shown in the figures) and because the size of the projections 402 relative to the groove 372, the outer floating element 328 can rotate (clockwise in FIG. 28B) relative to the knobbed, rigid shaft 326 to be in a position to engage the outside of the vessel. See, e.g., FIGS. 30 and 31.

Figure 29:
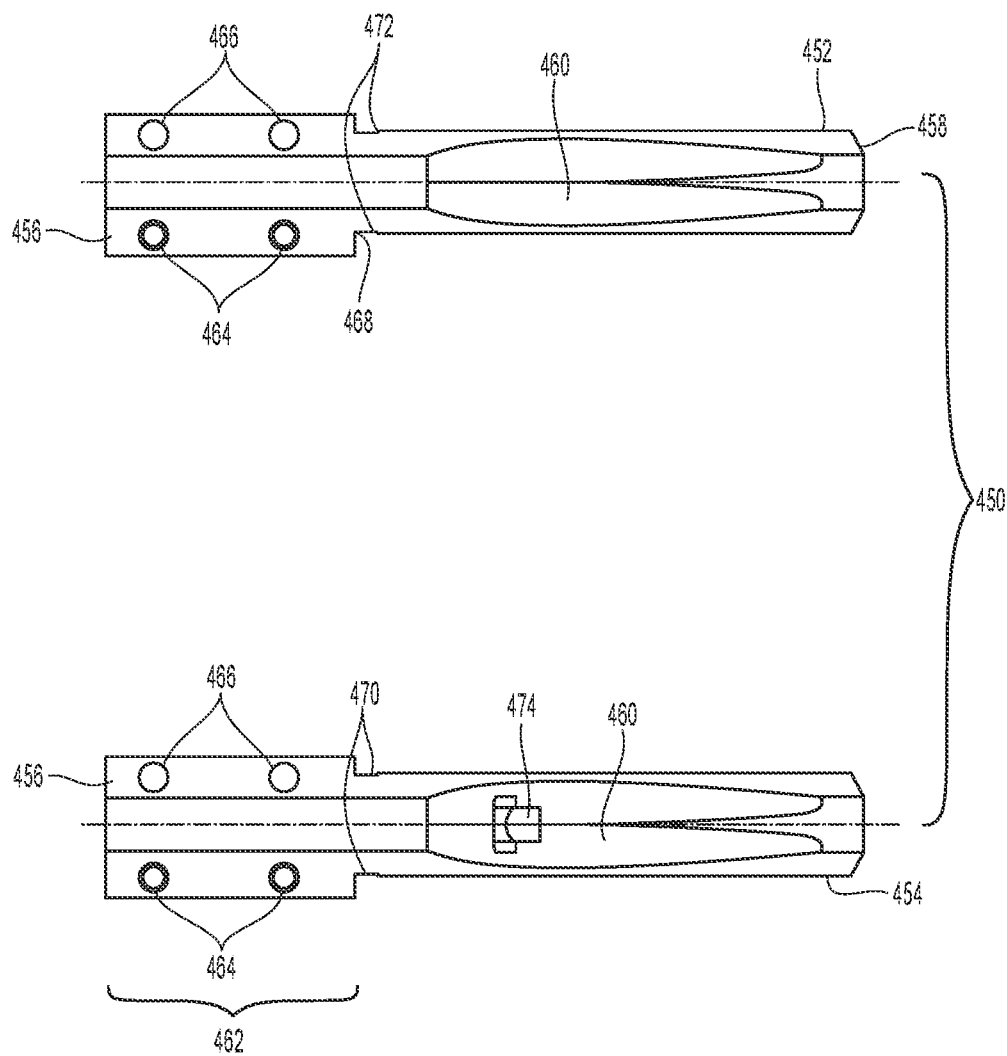
FIG. 29 is an exploded, perspective view of the inserter for use with the seal assembly of FIG. 20A.
Figure 30:
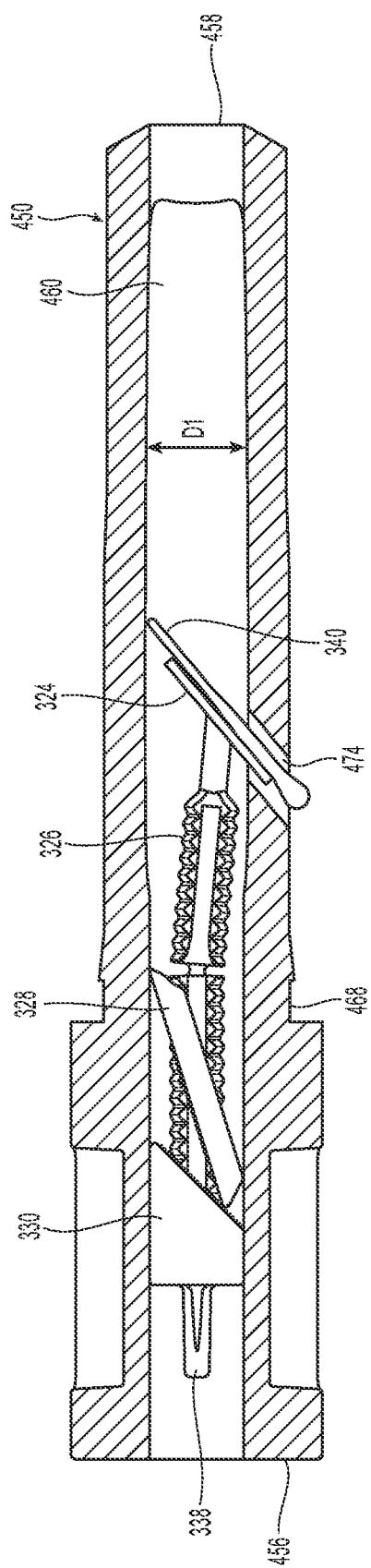
FIG. 30 is a cross section view of the seal assembly constrained in the inserter of FIG. 29.
Figure 31:
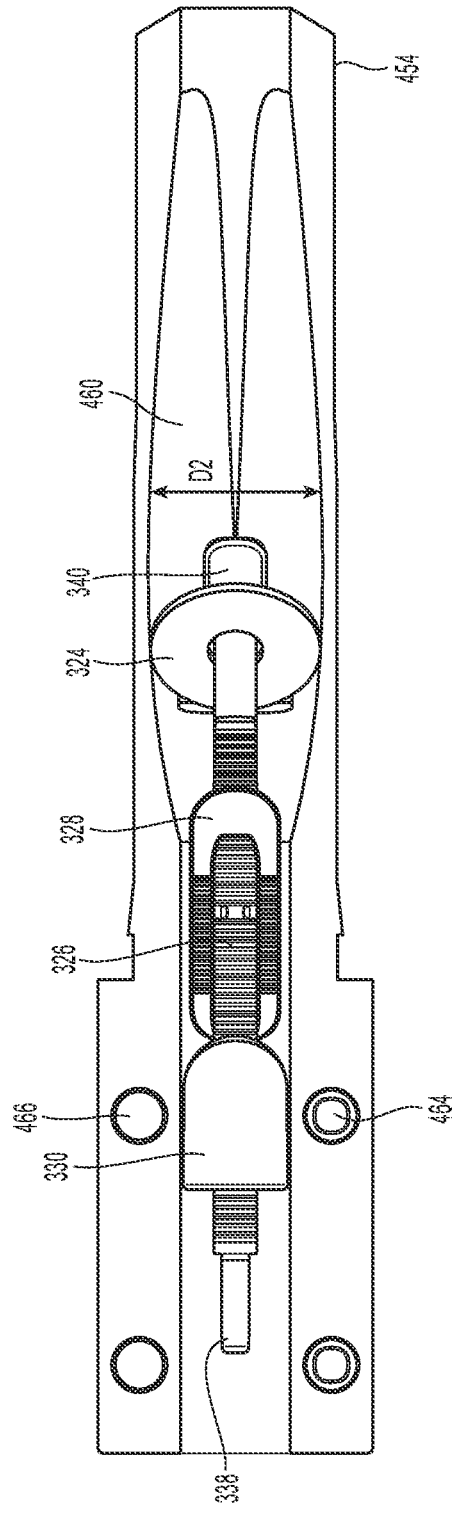
FIG. 31 is a top view of the seal assembly in the bottom portion of the inserter of FIG. 29.
Figure 32:
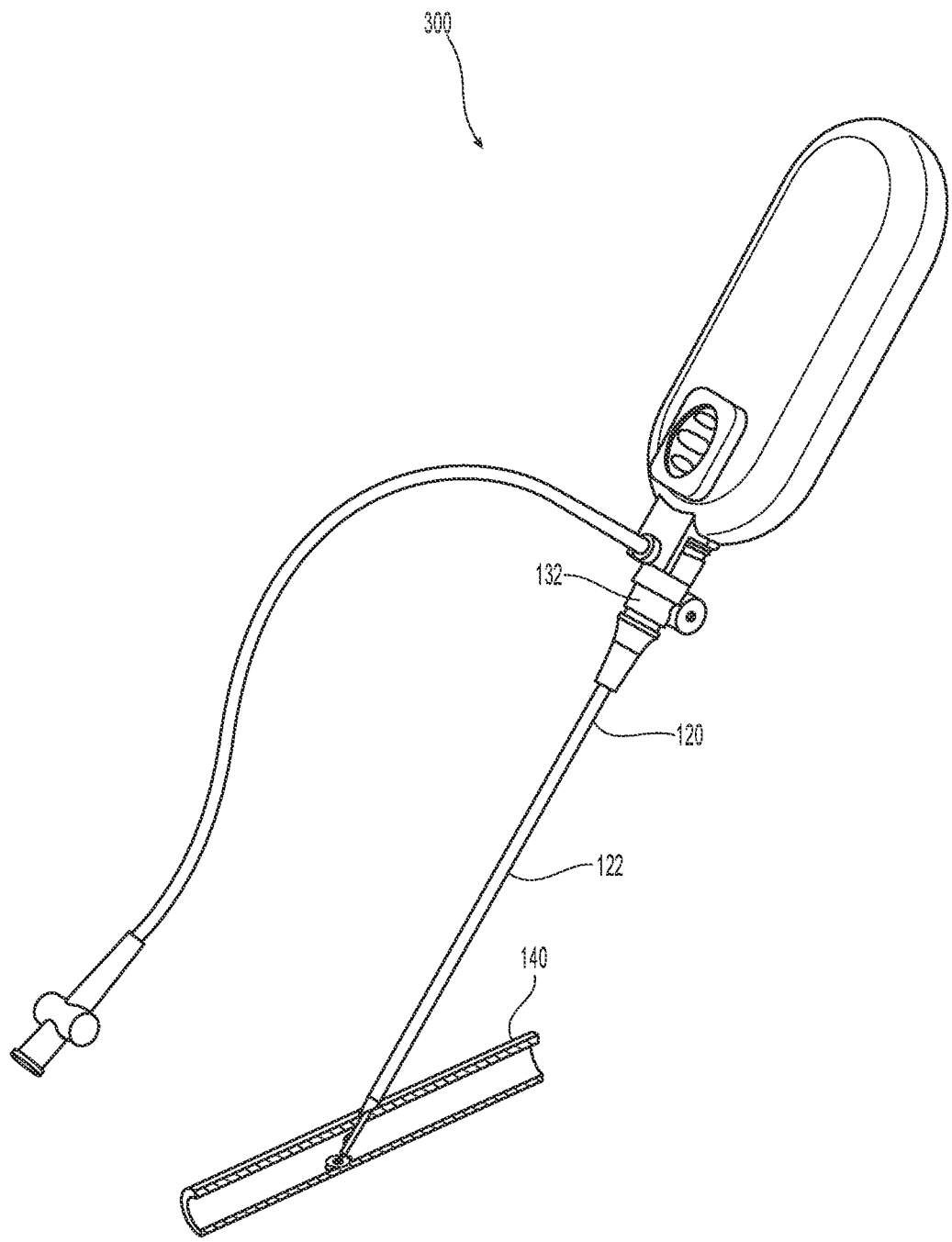
FIG. 32 is a perspective view of the sealing device inserted into a blood vessel.
Figure 33:
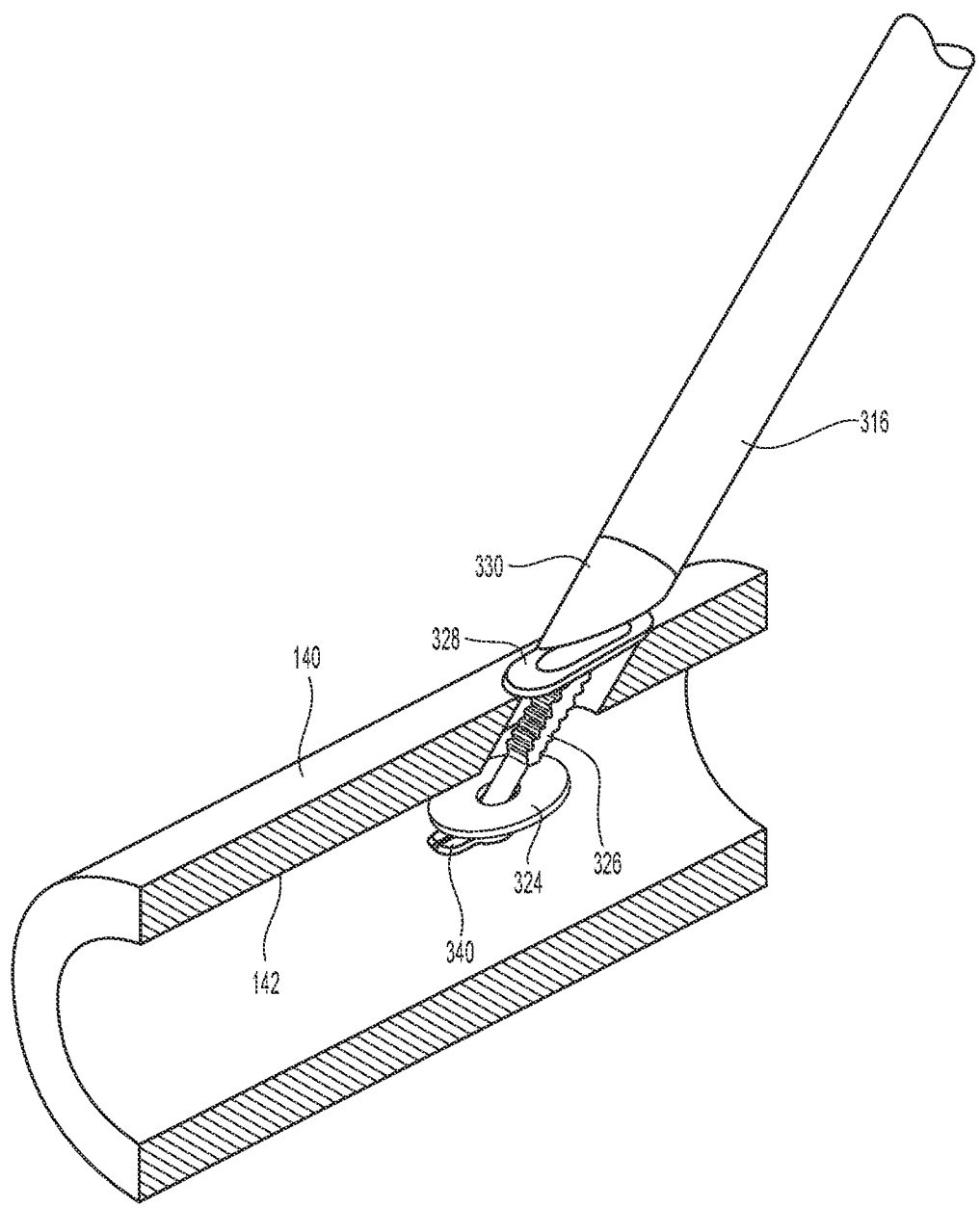
FIG. 33 is partial cross section view of a vessel with the sealing device inserted therein.
Figure 34:
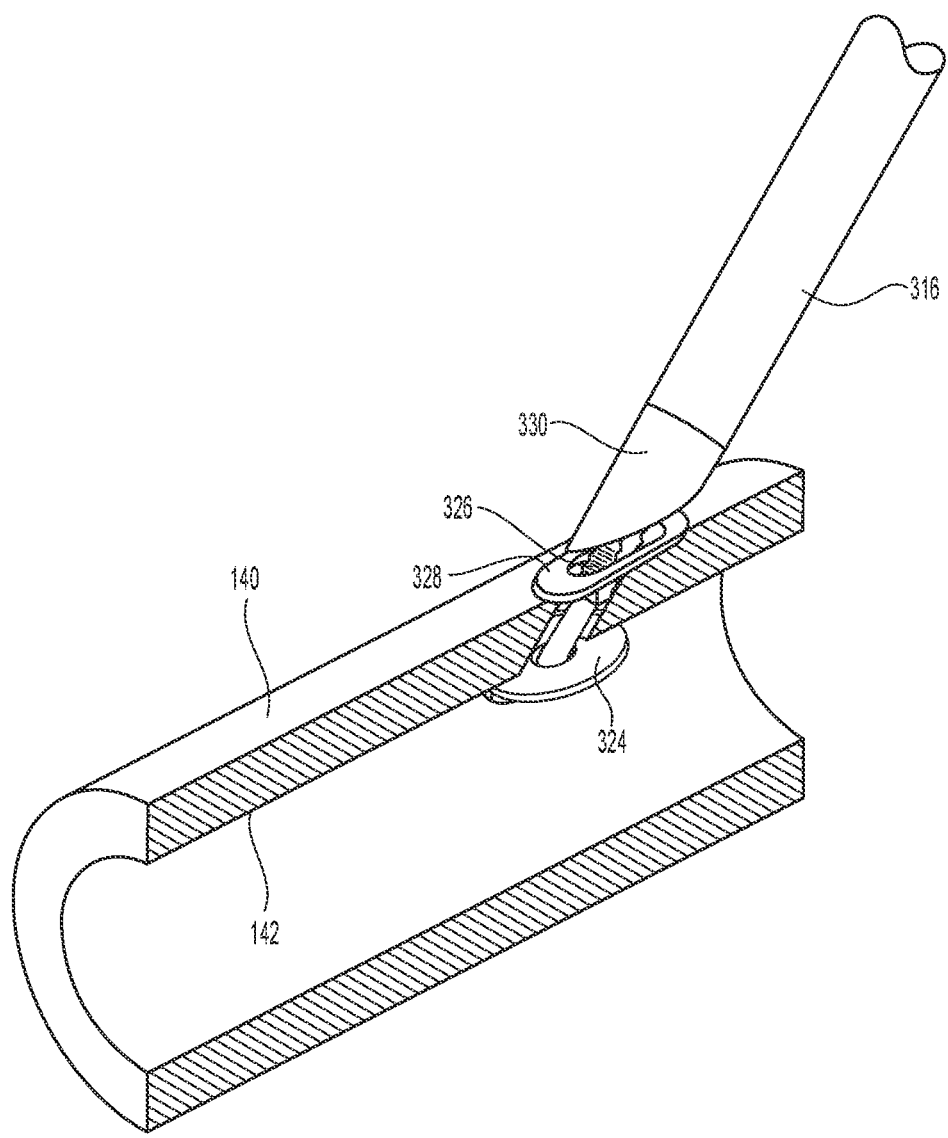
FIG. 34 is perspective view of the sealing device inserted into the blood vessel just before the sealing device is activated.

An inserter 450 is illustrated in FIGS. 29-31. The embodiment of the inserter 450 illustrated has a first portion 452 and a second portion 454, which are illustrated as a top half and a bottom half. Naturally, the portions 452,454 could have other names (e.g., side portions) and still fall within the scope of the present invention. The inserter 450 has a proximal end 456 and a distal end 458. When the portions 452,454 are assembled, a longitudinal opening 460 is created that extends through the inserter 450. The inserter 450 preferably has at the proximal end 456 a proximal section 462 that has a constant diameter outer surface and a constant diameter for the longitudinal opening 460 at the proximal section 462. The proximal section 462 of each of the portions 452,454 has a number of projections 464 and openings 466. The projections 464 of one portion 452,454 correspond to the openings 466 of the other portion 452,454, thereby allowing the two portions 452,454 to be brought together and aligned for use. Forward of the proximal section 462 is a reduced diameter area 468, which then increases in diameter at 470 creating a shoulder 472 before tapering back down to a smaller outer diameter at the distal end 458.

The longitudinal opening 460 in inserter 450 allows for the seal assembly 320 to be loaded therein, sterilized, stored, and then used by a doctor. Typically, if a seal assembly is contained within a confined space and then sterilized, the sterilization causes the seal assembly to maintain the configuration in which it is sterilized. Even if the material normally was some shape memory (allowing the material to spring back to its original shape or configuration), the sterilization has been found by the inventor to prevent the materials from returning to their original configuration. Thus, the current inserter 450 allows for the seal assembly 320 to be loaded without any real change in configuration. The longitudinal opening 460 has been designed to hold the first sealing element 322, a flexible member 324, a knobbed rigid shaft 326, an outer floating element 328, and a second sealing element 330 without this issue. To do so, however, the portion 454 has an aperture 474 to allow for the heel 356 of the distal section 340 to be disposed therein. While the aperture 474 is illustrated as extending through the portion 454, it is possible that there only be a depression, groove, or dimple that does not penetrate all the way through the portion 454.

Turning to FIG. 30, a cross section of the inserter 450 with the seal assembly 320 disposed therein illustrates the position of the seal assembly 320 within the inserter 450. As should be clear, the cross section is through the center of both portions 452,454. It should also be noted that the distance D1 of between the two portions 452,454 of the longitudinal opening 460 is generally constant. The position of the outer floating element 328 relative to the knobbed, rigid shaft 326 and the position of the flexible member 324 relative to the distal section 340 allow the inserter to have a minimum size.

FIG. 31 illustrates the seal assembly 320 within the inserter 450 from above the inserter 450. In this view, it is clear that the diameter D2 of the longitudinal opening 460 is larger in the horizontal plane; allowing the flexible member 324 to hold its original configuration. The longitudinal opening 460 at the proximal section 462 is also sized to allow the outer floating element 328 and the second sealing element 330 to pass therethrough. The longitudinal opening 460 at the distal end 458 is smaller than the diameter D2, but the flexible member 324 and the distal section 340 can be deformed and then return to their original shape for use in the patient.

Figure 35:
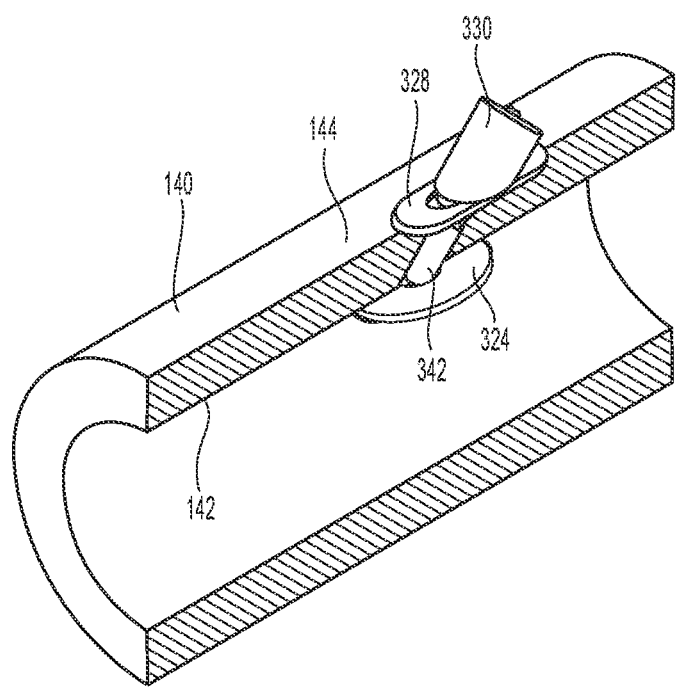
FIG. 35 is a perspective view of the seal assembly blocking the opening in the blood vessel after activation of the sealing device.
Figure 36:
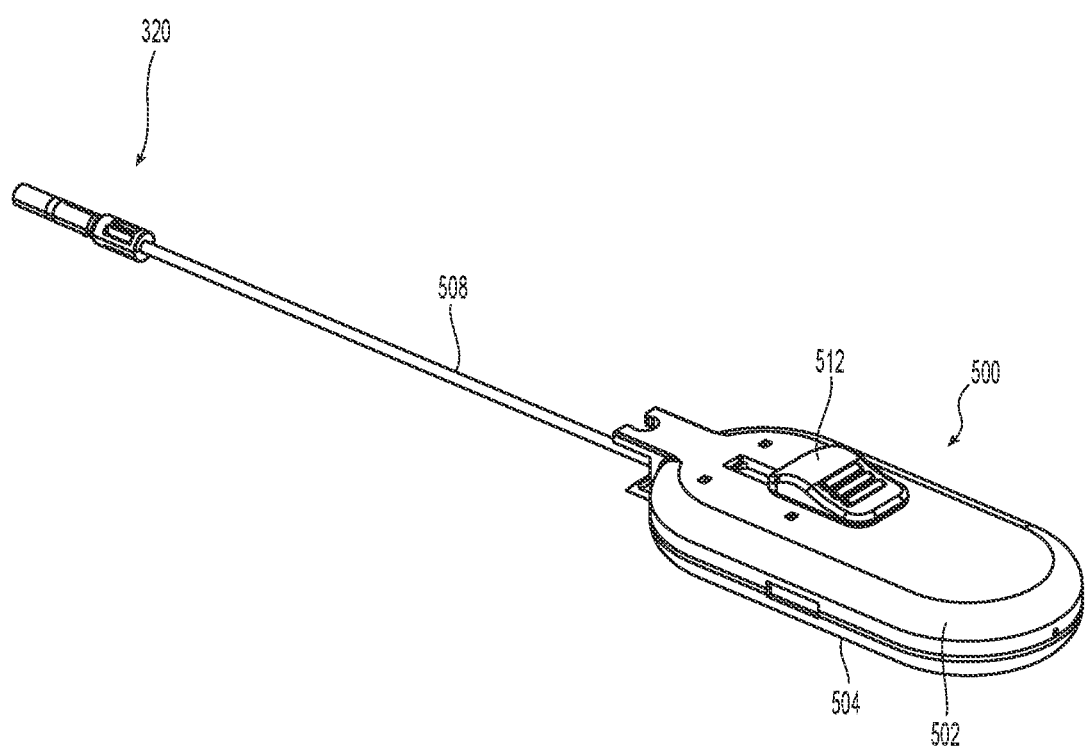
FIG. 36 is a perspective view of another embodiment of a sealing device according to the present invention.
Figure 37:
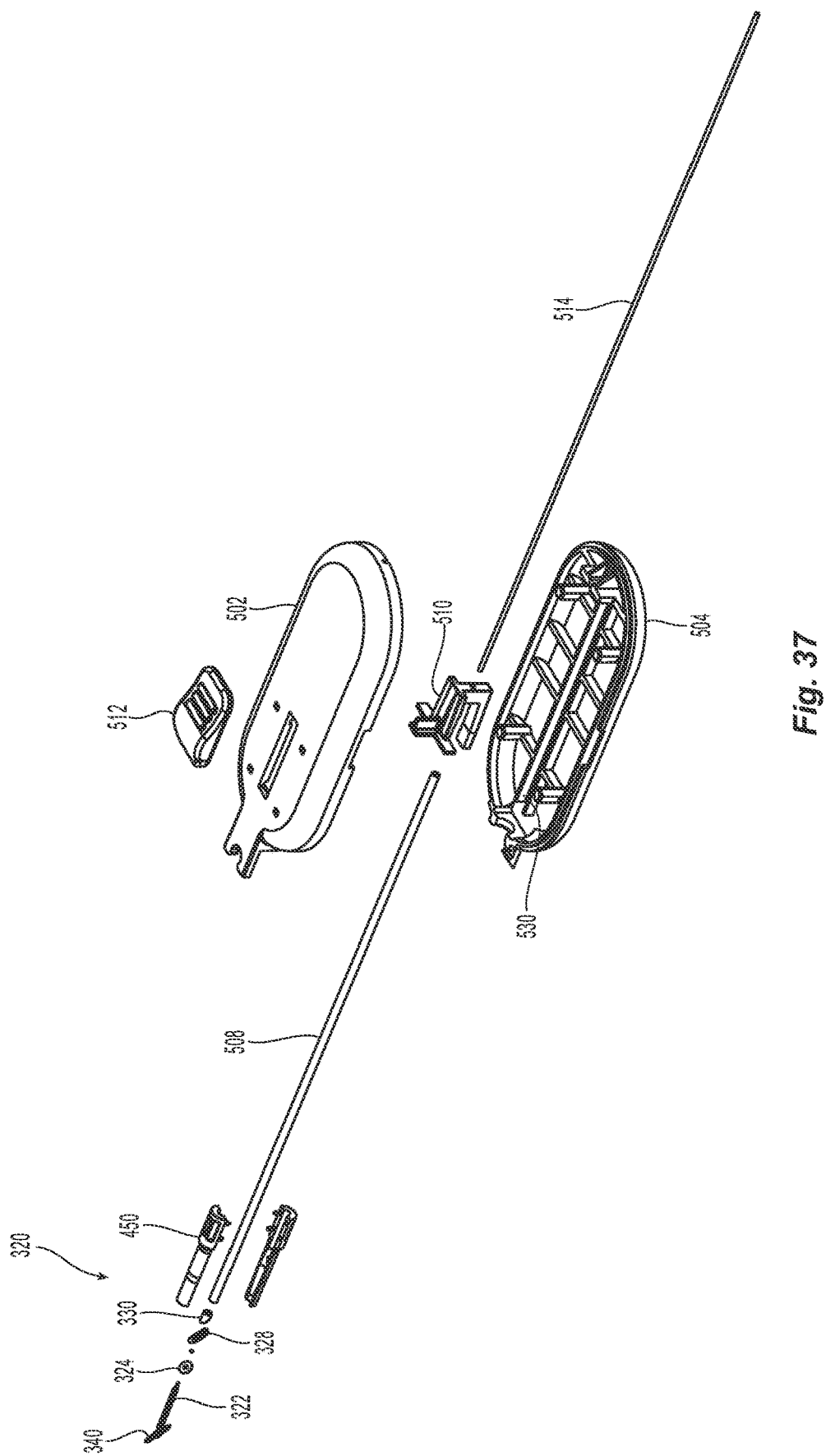
FIG. 37 is an exploded perspective view of the sealing device in FIG. 36.

A method of using the current invention in conjunction with FIGS. 32-35 is as follows: The device 300, and in particular the seal assembly 320 is inserted into inserter 450 that surrounds seal assembly 320 such that seal assembly 320 can pass through sheath valve 132 and to the sheath 120. This allows for the simultaneous removal of the device 300 and the sheath 120, if the sheath is not removed prior to the activation of the automatic mechanism. Inserting pusher 316 through sheath 120, including valve 132 and cannula 122, causes at least a portion of seal assembly 320 to exit the distal end of cannula 122 and into blood vessel 140. See FIG. 32. The sheath 120 may then be removed from the device 300. Pulling on the closure device 300, the flexible member 324 and the distal portion 340 of first sealing element 322 engages the interior blood vessel wall 142. See FIG. 34. This would also remove the second sealing element 330, the outer floating element 328, and the pusher 316 from within the blood vessel 140. Continuing to pull on the sealing assembly 320, and therefore flexible shaft 318, triggers the automatic mechanism 150 in the closure device 300, which pushes pusher 316, and which in turn pushes second sealing element 330, and the outer floating element 328 distally such that the outer floating element 328 is in contact with outer wall of blood vessel 140. This will sandwich the outer floating element 328, the blood vessel 140 and the flexible member 324 between the first and second sealing elements 322, 330 such that the opening in blood vessel 140 is hemostatically sealed, as shown in FIG. 35.

Another embodiment of a closure device 500 is illustrated in FIGS. 36-47. In this embodiment, the closure device 500 is not automatic, but a semi-automatic device to seal the vessel. The closure device 500 has a top cover 502 and a bottom cover 504 that are connected to one another. The top cover 502 and the bottom cover 504 house the pushing assembly 506. The pushing assembly 506 includes a pushing rod 508, a pusher 510 and a button 512. As explained in more detail below, the button 512 is used to move the pusher 510, which is fixedly attached to the pushing rod 508, to activate the seal assembly 320.

The seal assembly 320 may be and is preferably the same as the seal assembly 320 discussed in detail above with regard to FIGS. 20A-31. As is visible in FIG. 37, the seal assembly 320 has a first sealing element 322, a flexible member 324, a knobbed rigid shaft 326, an outer floating element 328, and a second sealing element 330. It is possible that the first sealing element 322 and the flexible member 324 are a single element—that is a one single-piece component. There may be other configurations of the seal assembly as well, as discussed above. Also in FIGS. 24 and 25 is a cross section of the knobbed, rigid shaft 326 at the weakened notch feature 336. The weakened notch feature 336 has a smaller cross section than any other portion of the knobbed rigid shaft 326. This allows for the knobbed, rigid shaft 326 to be broken at this point upon activation of the closure device 500, as discussed in more detail below, by exerting a force in the direction of the length of the knobbed, rigid shaft 326, causing the knobbed, rigid shaft 326 to break at the weakened notch feature 336. In order to prevent the weakened notch feature 336 from breaking prematurely, a c-shaped ring may be clipped into the weakened notch feature 336 as noted above. The width of notch feature 336 is sized to equal the space between knobs 362 so that second seal 328 can easily transition over notch feature 336 upon activation of device 300. The c-shaped ring prevents the knobbed, rigid shaft 326 from being tilted off center and breaking prematurely.

Figure 38:
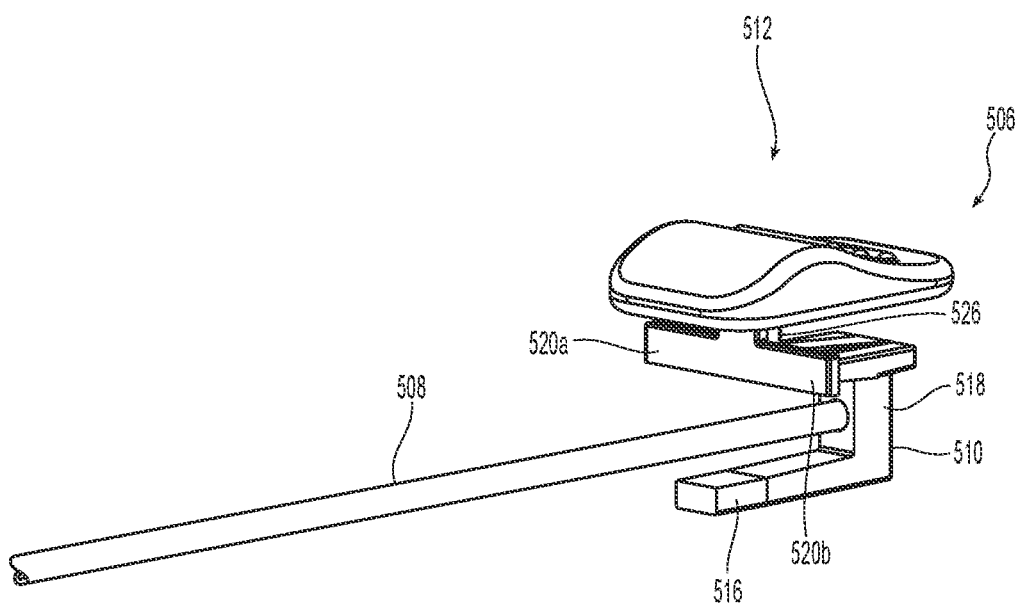
FIG. 38 is a perspective view of the pushing assembly of the sealing device in FIG. 36.
Figure 39:
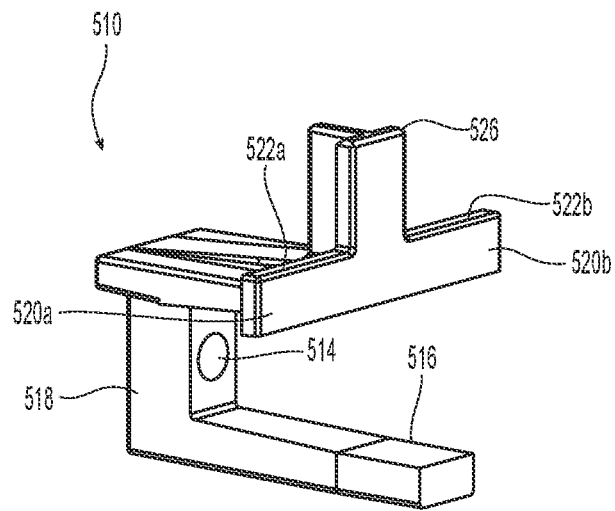
FIG. 39 is a perspective view of the pusher of the pushing assembly of the sealing device in FIG. 36.
Figure 40:
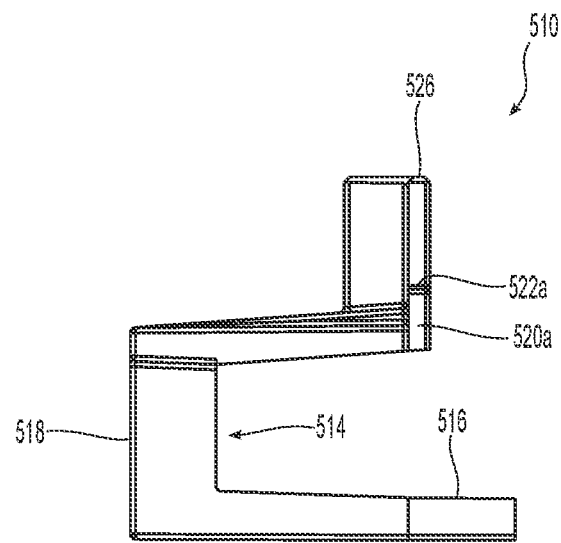
FIG. 40 is an elevation view of the pusher in FIG. 39.

Referring to FIGS. 38-40 the structure of the pushing assembly 506 will be discussed. The pusher 510 has an opening 514 that receives and can have secured therein the pushing rod 508. Thus, as the pusher 510 is moved, so too is the pushing rod 508. The pusher 510 has a foot 516 that extends in a forward direction (toward the seal assembly 320) and is connected by a central portion 518 to two arms 520a and 520b. Each of the arms 520a and 520b has a top surface 522a and 522b, respectively. The pusher 510 also has a button extension 526 that can receive the button 512. As noted in the figures, the surface 522a and 522b of the arms 520a, 520b are perpendicular to the foot 516.

Figure 41:
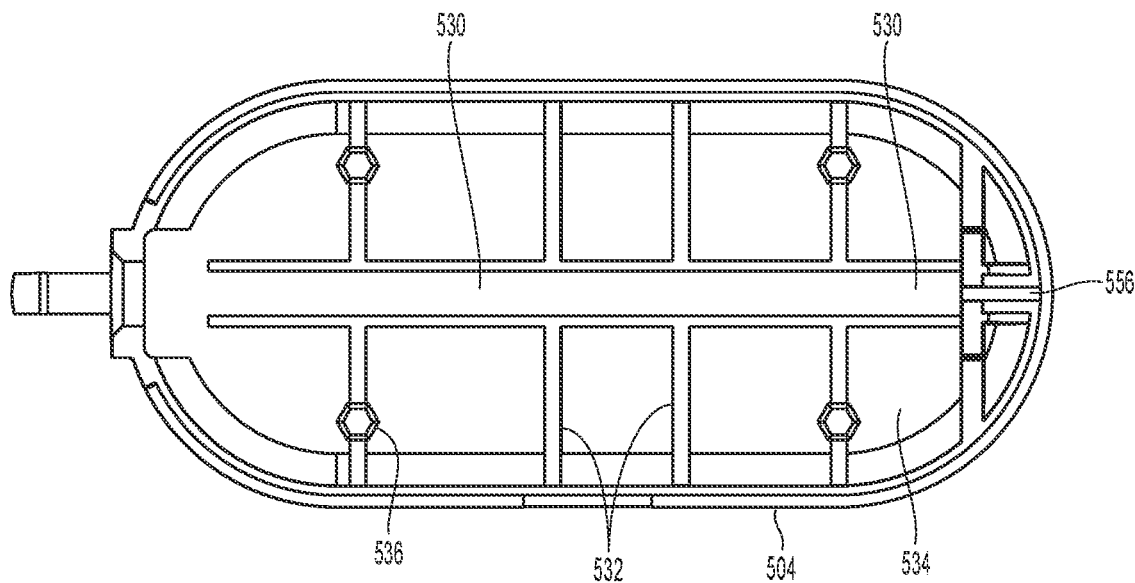
FIG. 41 is a plan view of the bottom cover of the sealing device in FIG. 36.
Figure 42:
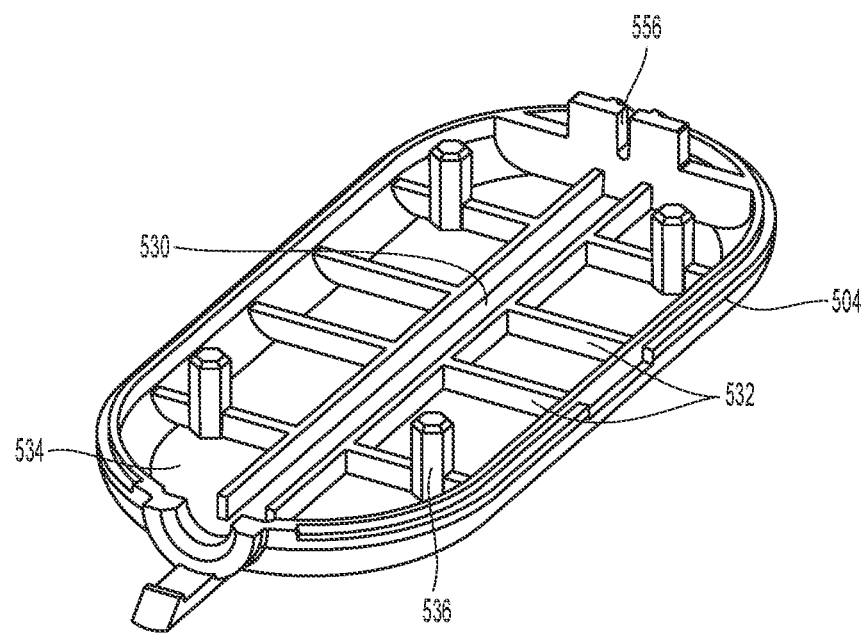
FIG. 42 is perspective view of the bottom cover of the sealing device in FIG. 36.

Turning to FIGS. 41 and 42, the bottom cover 504 has a central channel 530 in which the foot 516 of the pusher 510 can slide or ride in during operation. The bottom cover 504 has a plurality of ribs 532 to provide structural integrity that extend from the inside surface 534. There are also posts 536 to support the top cover 502.

Figure 43:
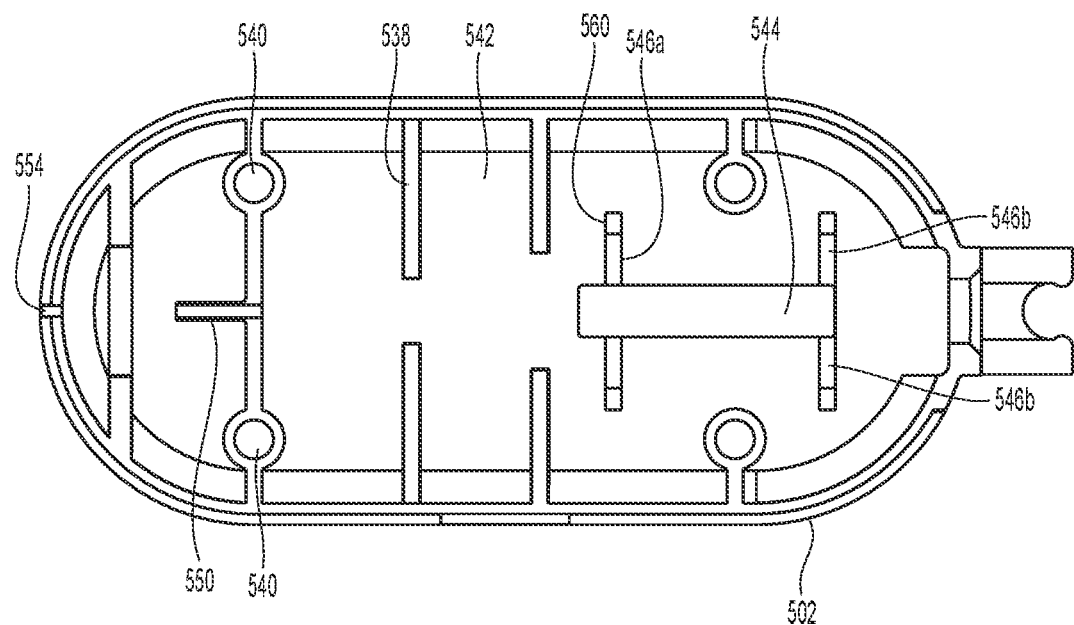
FIG. 43 is a plan view of the top cover of the sealing device in FIG. 36.
Figure 44:
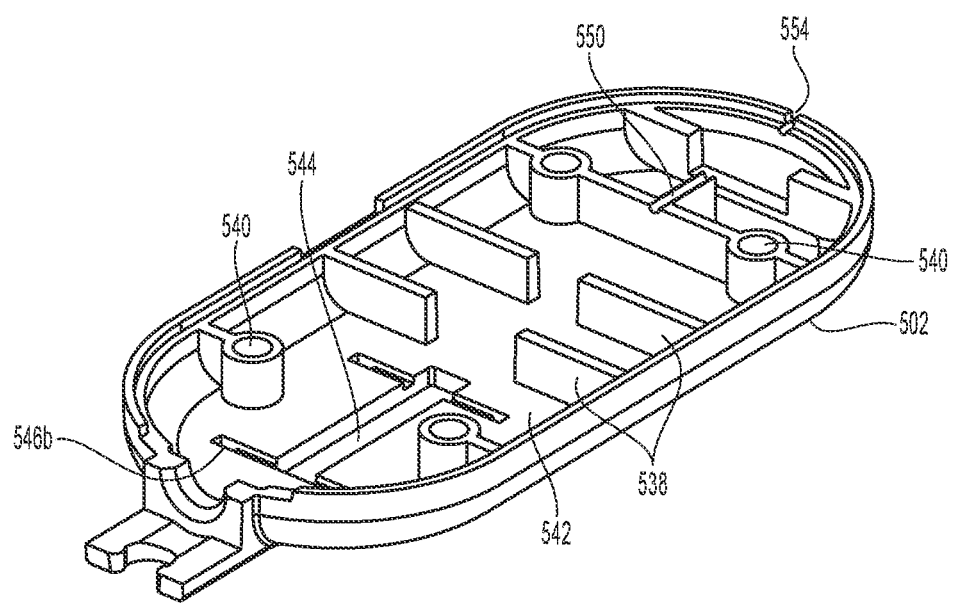
FIG. 44 is a perspective view of the top cover of the sealing device in FIG. 36.
Figure 45:
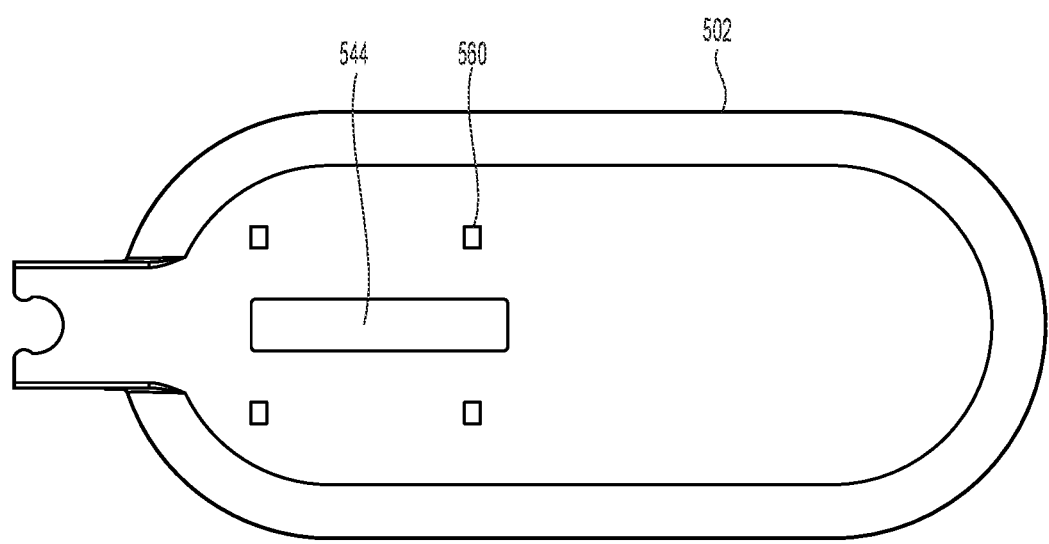
FIG. 45 is a plan view of the outside of the top cover of the sealing device in FIG. 36.
Figure 46:
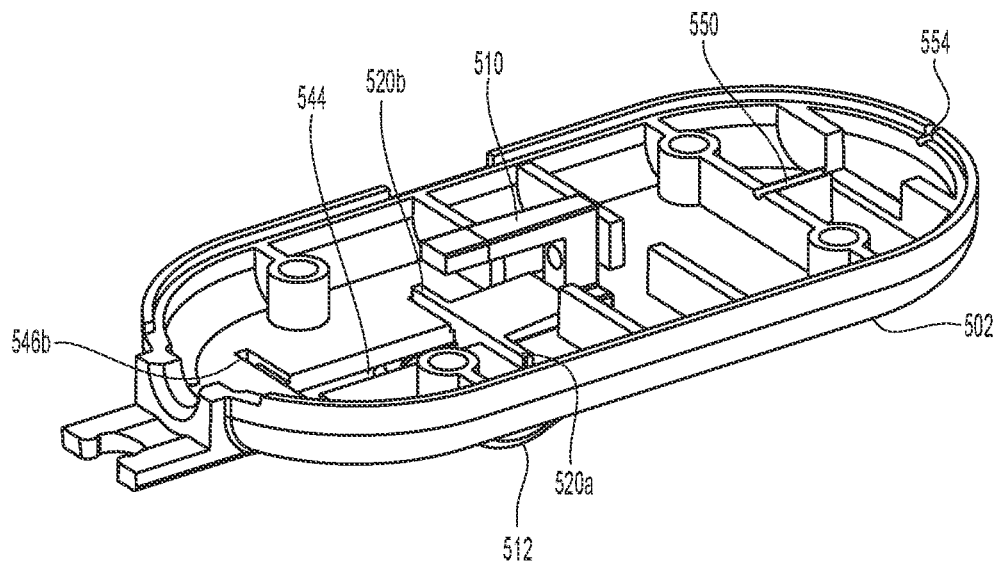
FIG. 46 is a perspective view of the top cover of the sealing device in FIG. 36 with the pusher disposed therein.

The top cover 502 is illustrated in more detail in FIGS. 43 and 44. The top cover 502 has a plurality of ribs 538 also to provide structural integrity and a number of post receptacles 540 to receive the posts 536 from the bottom cover 504. These structures are preferably attached to the inside surface 542. The top cover 502 also includes an opening 544 through which the button extension 526 and button 512 project to the outside of the top cover 502. Extending outwardly to the sides of the top cover 502 and on either side of the opening 544 are slots 546a to receive the top surfaces 522a and 522b of the two arms 520a and 520b. There are another two slots 546b at the other end of the opening 544. As noted, there are four such slots (two of 546a and two of 546b) in the illustrated top cover 502. However, there could just be two slots, one at each end of the opening 544 in the top cover 502, rather than the two that are illustrated at each end of the opening 544.

The top cover 502 also includes a slot 550 to support a shaft 552 that is connected to the seal assembly 320 as illustrated as discussed above. The shaft 552 (see FIG. 37) can be secured to the slot 550 as well as a second slot 554 at the rear end of the top cover 502. Corresponding thereto is also a slot 556 at the back end of the bottom cover 504. See FIGS. 41 and 42.

Returning to FIGS. 43 and 45, there are four holes 560 in the top cover 504 that function as an indicator as to the position of the two arms 520a and 520b. Since the holes 560 are at the end of the slots 546a and 546b, it is possible to know where the two arms 520a and 520b are before using the device 500. Additionally, the four holes 560 need not be at the end of the slots 546a, 546b, but could be anywhere along the slots as long as they are not blocked by the button 512.

Having described the components, the operation of the device 500 will now be explained. First, it is noteworthy that the interior space between the top cover 502 and the bottom cover 504 is slightly less than the relaxed position of the pusher 510. Thus, when the pusher 510 is secured within the device 500, there is a slight compression of the pusher 510—pushing the arms 520a and 520b toward the foot 516. When the pusher 510 is aligned with the slots 546a and 546b, the arms 520a and 520b are biased into the slots 546a, 546b. To move the button 512 and the entire pushing assembly 506 forward, the user must push down and forward on the button 512. Some force will be needed to move the arms 520a and 520b out of the first set of slots 546a. The pushing assembly 506 will move forward to the second set of slots 546b, moving the pushing rod 508 and the second portion (second sealing element 330) of the seal assembly 320 toward the first portion (first sealing element 322). As the second portion of the seal assembly 320 is pushed toward the first portion and sandwiches the blood vessel between the first and second portions of the seal assembly 320, there be an increased force required to push the pushing assembly 508 toward the first portion of the seal assembly 320. When that force equals the force required to break the knobbed, rigid shaft 326 at the weakened notch feature 336, the device 500 will be separated from the seal assembly—preventing any more pressure from being applied to the seal assembly 320. Thus, the force applied to sealing the blood vessel is controlled and limited by the force required to break the knobbed, rigid shaft 326. As a result, the amount of pressure applied to sealing the blood vessel is tightly controlled by the design of the weakened notch feature 336. Thus, too much pressure cannot be applied to seal assembly and if too little pressure is applied, then the device 500 cannot be removed until the required amount of pressure is applied.

Figure 47:
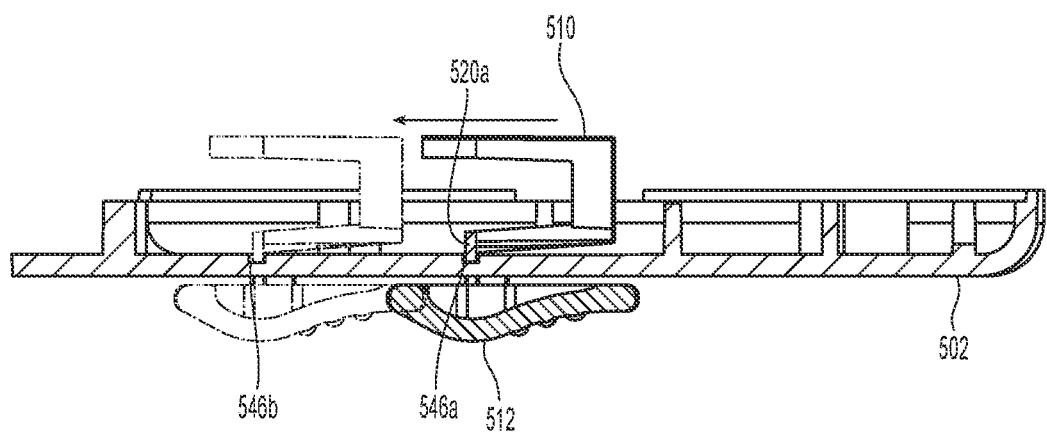
FIG. 47 is a cross section of the top cover and the pusher showing the pusher in two different positions.

It should also be noted that the second set of slots 546b will stop the movement of the pushing rod 508, which coincides with the distance that the pushing rod 508 and the second portion of the seal assembly 320 must move to seal the blood vessel. See FIG. 47 showing the movement of the pushing assembly 508.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

We claim:

1. A device for sealing an opening in the wall of a blood vessel, the blood vessel having an interior wall surface, an exterior wall surface, and a lumen, the device comprising:
 a pushing rod, the pushing rod having an opening therealong;
 a shaft disposed within at least a portion of the opening of the pushing rod;
 a pusher, the pusher fixedly attached to the pushing rod;
 a bottom cover and a top cover, a button extending through an opening in the top cover and engaging the pusher; and
 a seal assembly having a first portion and a second portion, the seal assembly operatively attached at the first portion to the distal end of the shaft, the seal assembly configured to engage the interior wall surface and the exterior wall surface of the blood vessel,
 wherein the pushing rod operatively engages the seal assembly at the second portion and is movable relative to the shaft, the pushing rod moving from a first position to a second position in response to the button moving distally causing the first portion and the second portion of the seal assembly to move relative to one another, and
 wherein the pusher has a foot and two arms, the arms engaging a first slot in the top cover at a proximal end of the opening in the top cover in a first status and a second slot in the top cover at a distal end of the opening in the top cover in a second status.

2. The device according to claim 1, wherein the shaft is attached to at least one of the top and the bottom cover.

3. The device according to claim 1, wherein a predetermined force on the button causes the arms to move out of the first slot and into the second slot.

4. The device according to claim 1, wherein the pusher is integral with the pushing rod.

5. A device for sealing an opening in the wall of a blood vessel, the blood vessel having an interior wall surface, an exterior wall surface, and a lumen, the device comprising:

a top cover and a bottom cover, the top cover having an opening therein;

a pusher with arms extending in a first direction and a foot extending in a second direction, the arms engaging a first slot in the top cover at a proximal end of the opening in the top cover in a first position and a second slot in the top cover at a distal end of the opening in the top cover in a second position;

a shaft extending between a proximal end and a distal end, the shaft extending within a portion of a pushing rod;

a seal assembly having a first portion and a second portion, the seal assembly operatively attached at the first portion to the distal end of the shaft, the seal assembly configured to engage the interior wall surface and the exterior wall surface of the blood vessel; and the pushing rod operatively engaging the seal assembly at the second portion and movable relative to the shaft, the pusher moving the pushing rod from a first position to a second position in response to a button associated with the pusher thereby causing the first portion and the second portion of the seal assembly to move relative to one another.

6. The device according to claim 5, wherein the first and second directions are perpendicular to one another.

7. The device according to claim 5, wherein the foot is disposed within a channel in the bottom cover.

8. The device according to claim 7, wherein the opening in the top cover and the channel in the bottom cover are aligned with one another.

9. A device for sealing an opening in the wall of a blood vessel, the blood vessel having an interior wall surface, an exterior wall surface, and a lumen, the device comprising:

a pushing assembly;

a shaft disposed within at least a portion of the pushing assembly;

a bottom cover and a top cover, a button extending through an opening in the top cover and engaging a portion of the pushing assembly; and a seal assembly having a first portion and a second portion, the seal assembly operatively attached at the first portion to the distal end of the shaft, the seal assembly configured to engage the interior wall surface and the exterior wall surface of the blood vessel, wherein the pusher has arms extending in a first direction and a foot extending in a second direction, the arms engaging a first slot in the top cover at a proximal end of the opening in the top cover in a first position and a second slot in the top cover at a distal end of the opening in the top cover in a second position wherein the pushing assembly operatively engages the seal assembly at the second portion, the pushing assembly moving from the first position to the second position causing the first portion and the second portion of the seal assembly to move relative to one another to cause the seal assembly to break from the device.

10. The device according to claim 9, wherein the pushing assembly comprises a pushing rod, a pusher fixedly attached to the pushing rod and the button.

* * * * *